US008465727B2

(12) United States Patent
Bowser

(10) Patent No.: US 8,465,727 B2
(45) Date of Patent: Jun. 18, 2013

(54) BIOMARKERS FOR THE DIAGNOSIS OF ALS

(75) Inventor: Robert P. Bowser, Cranberry Township, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 110 days.

(21) Appl. No.: 12/899,235

(22) Filed: Oct. 6, 2010

(65) Prior Publication Data

US 2011/0086894 A1    Apr. 14, 2011

Related U.S. Application Data

(60) Provisional application No. 61/249,083, filed on Oct. 6, 2009, provisional application No. 61/311,144, filed on Mar. 5, 2010.

(51) Int. Cl.
| | |
|---|---|
| *A61B 5/145* | (2006.01) |
| *G01N 33/48* | (2006.01) |
| *G01N 33/49* | (2006.01) |
| *A61K 35/30* | (2006.01) |
| *A61P 25/02* | (2006.01) |
| *A61P 25/28* | (2006.01) |

(52) U.S. Cl.
USPC ............... 424/9.1; 435/4; 435/7.1; 435/7.92; 702/19; 702/22; 702/23; 514/17.7; 514/18.2

(58) Field of Classification Search
None
See application file for complete search history.

(56) References Cited

U.S. PATENT DOCUMENTS

2006/0178306 A1    8/2006    Bowser

OTHER PUBLICATIONS

Petzold et al., J Immunol Methods, 278:179-190, 2003.*
Boylan et al., J Neurochemistry, 111:1182-1191, epublished Sep. 18, 2009.*
Desport et al., Am J Clin Nutr, 74:328-334, 2001.*
Goldknopf et al., Biochemical and Biophysical Research Communications, 342: 1034-1039, 2006.*
Ackerley, et al., "Neurofilament heavy chain side arm phosphorylation regulates axonal transport of neurofilaments", J Cell Biol, 161:489-495 (2003).
Al-Chalabi, et al., "Deletions of the heavy neurofilament subunit tail in amyotrophic lateral sclerosis", Hum Mol Genet, 8:57-164 (1999).
Anderson, et al., "The phosphorylated axonal form of the neurofilament subunit NF-H (pNF-H) as a blood biomarker of traumatic brain injury", J Neurotrauma., 25:1079-1085 (2008).
Annunziata and Volpi, "High levels of C3c in the cerebrospinal fluid from amyotrophic lateral sclerosis patients", Acta Neurol Scand., 72:61-64 (1985).
Bowser and Lacomis, "Applying proteomics to the diagnosis and treatment of ALS and related diseases", Muscle Nerve, 40:753-762 (2009).

Boylan, et al., "Immunoreactivity of the phosphorylated axonal neurofilament H subunit (pNF-H) in blood of ALS model rodents and ALS patients: evaluation of blood pNF-H as a potential ALS biomarker", J Neurochem., 111:1182-1191 (2009).
Brettschneider, et al., "Axonal damage markers in cerebrospinal fluid are increased in ALS", Neurology, 66:852-856 (2006).
Brooks, "El Escorial World Federation of Neurology criteria for the diagnosis of amyotrophic lateral sclerosis, Subcommittee on Motor Neuron Diseases/Amyotrophic Lateral Sclerosis of the World Federation of Neurology Research Group on Neuromuscular Diseases and the El Escorial "Clinical limits of amyotrophic lateral sclerosis", workshop contributors", J Neurol Sci., 124 Suppl:96-107 (1994).
Cleveland and Rothstein, "From Charcot to Lou Gehrig: deciphering selective motor neuron death in ALS", Nat. Rev. Neurosci., 2:806-19 (2001).
Eikelenboom and Veerhuis, "The role of complement and activated microglia in the pathogenesis of Alzheimer's disease", Neurobiol Aging, 17:673-680 (1996).
Gelinas, "Conceptual approach to diagnostic delay in ALS: a United States perspective", Neurology, 53:S17-19; discussion S20-11 (1999).
Goldknopf, et al., "Complement C3c and related protein biomarkers in amyotrophic lateral sclerosis and Parkinson's disease", Biochem Biophys Res Commun., 342:1034-1039 (2006).
Groeneveld, et al., "A randomized sequential trial of creatine in amyotrophic lateral sclerosis", Annals of Neurology, 53:437-45 (2003).
Guy, et al., "Phosphorylated neurofilament heavy chain is a marker of neurodegeneration in Leber hereditary optic neuropathy (LHON)", Mol Vis., 14:2443-2450 (2008).
Haverkamp, "Natural history of amyotrophic lateral sclerosis in a database population. Validation of a scoring system and a model for survival prediction", Brain, 118 ( Pt 3):707-719 (1995).
Kawamata, et al., "Immunologic reactions in amyotrophic lateral sclerosis brain and spinal cord tissue", Am J Pathol., 140:691-707 (1992).
Kuhle, "Increased levels of inflammatory chemokines in amyotrophic lateral sclerosis", Eur J Neurol., 16:771-774 (2009).
Lewis, et al., "Detection of phosphorylated NF-H in the cerebrospinal fluid and blood of aneurysmal subarachnoid hemorrhage patients", J Cereb Blood Flow Metab, 28:1261-71 (2008).
Mares, et al., "The assessment of beta amyloid, tau protein and cystatin C in the cerebrospinal fluid: laboratory markers of neurodegenerative diseases", Neurol Sci., 30:1-7 (2009).
McGeer and McGeer,"Inflammation and neurodegeneration in Parkinson's disease", Parkinsonism Relat Disord., 10 Suppl 1:S3-7 (2004).

(Continued)

*Primary Examiner* — Jeffrey Stucker
*Assistant Examiner* — Stacey N MacFarlane
(74) *Attorney, Agent, or Firm* — Pabst Patent Group LLP

(57) ABSTRACT

Methods for determining the onset of ALS in a subject are provided. One method includes analyzing a sample obtained from the subject for the presence or amount of one or more biomarkers indicative of ALS. In a preferred embodiment, the biomarkers are one or more of the following: C-reactive protein (CRP), cystatin c, plasminogen, complement C3, Cys-Gly-transthyretin, and phosphorylated neurofilament heavy chain (pNFH). The sample is typically cerebral spinal fluid (CSF). The levels or concentrations of the biomarkers can be used to determine the onset of ALS, monitor the progression of ALS, or monitor the progression of a treatment for ALS.

21 Claims, 18 Drawing Sheets

OTHER PUBLICATIONS

Miller et al., "Riluzole for amyotrophic lateral sclerosis (ALS)/motor neuron disease (MND)", Amyotrophic Lateral Sclerosis & Other Motor Neuron Disorders, 4:191-206 (2003).

Mitchell, et al., "A CSF biomarker panel for identification of patients with amyotrophic lateral sclerosis", Neurology, 72:14-19 (2009).

Morita, et al., "Occurrence of complement protein C3 in dying pyramidal neurons in rat hippocampus after systemic administration of kainic acid", Neurosci Lett., 409:35-40 (2006).

Paladino, et al., "Cerebrospinal fluid tau protein is not a biological marker in amyotrophic lateral sclerosis", Eur J Neurol 16:257-261 (2009).

Petzold, et al., Longitudinal one-year study of levels and stoichiometry of neurofilament heavy and light chain concentrations in CSF in patients with multiple system atrophy. J Neurol Sci., 279:76-79 (2009).

Pijnenburg, et al., "CSF neurofilaments in frontotemporal dementia compared with early onset Alzheimer's disease and controls", Dement Geriatr Cogn Disord, 23:225-230 (2007).

Ranganathan, et al., "Proteomic profiling of cerebrospinal fluid identifies biomarkers for amyotrophic lateral sclerosis", J Neurochem., 95:1461-1471 (2005).

Reijn, et al., "CSF neurofilament protein analysis in the differential diagnosis of ALS", J Neurol, 256:615-619 (2009).

Rosen, et al., "A frequent ala 4 to val superoxide dismutase-1 mutation is associated with a rapidly progressive familial amyotrophic lateral sclerosis", Hum Mol Genet, 3:981-987 (1994).

Rosen, et al., "Mutations in Cu/Zn superoxide dismutase gene are associated with familial amyotrophic lateral sclerosis", Nature, 362:59-62 (1993).

Rothstein, "Current hypotheses for the underlying biology of amyotrophic lateral sclerosis", Ann Neurol, 65 Suppl 1:S3-9 (2009).

Rus and Niculescu, "The complement system in central nervous system diseases", Immunol Res., 24:79-86 (2001).

Ryberg and Bowser, "Protein biomarkers for amyotrophic lateral sclerosis", Expert Rev Proteomics, 5:249-262 (2008).

Subramaniam, et al., "Mutant SOD1 causes motor neuron disease independent of copper chaperone-mediated copper loading", Nat. Neurosci., 5;301-307 (2002).

Sussmuth, et al., "Amyotrophic lateral sclerosis: disease stage related changes of tau protein and S100 beta in cerebrospinal fluid and creatine kinase in serum", Neurosci Lett., 353:57-60 (2003).

Sussmuth, et al., "Tau protein in cerebrospinal fluid (CSF): a blood-CSF barrier related evaluation in patients with various neurological diseases", Neurosci Lett., 300:95-98 (2001).

Teunissen, et al., "Combination of CSF N-acetylaspartate and neurofilaments in multiple sclerosis", Neurology, 72:1322-1329 (2009).

Wild, et al., "Plasma neurofilament heavy chain levels in Huntington's disease", Neurosci Lett., 417:231-233 (2007).

WolBink, et al., "CRP-mediated activation of complement in vivo: assessment by measuring circulating complement-C-reactive protein complexes", J Immunol., 157:473-479 (1996).

Wong, et al., "Characterization of neuronal intermediate filament protein expression in cervical spinal motor neurons in sporadic amyotrophic lateral sclerosis (ALS)", J Neuropathol Exp Neurol., 59:972-982 (2000).

Woodruff, et al., "Role of complement in motor neuron disease: animal models and therapeutic potential of complement inhibitors", Adv Exp Med Biol., 632:143-158 (2008).

Yasojima, et al., "Up-regulated production and activation of the complement system in Alzheimer's disease brain", Am J Pathol., 154:927-936 (1999).

* cited by examiner

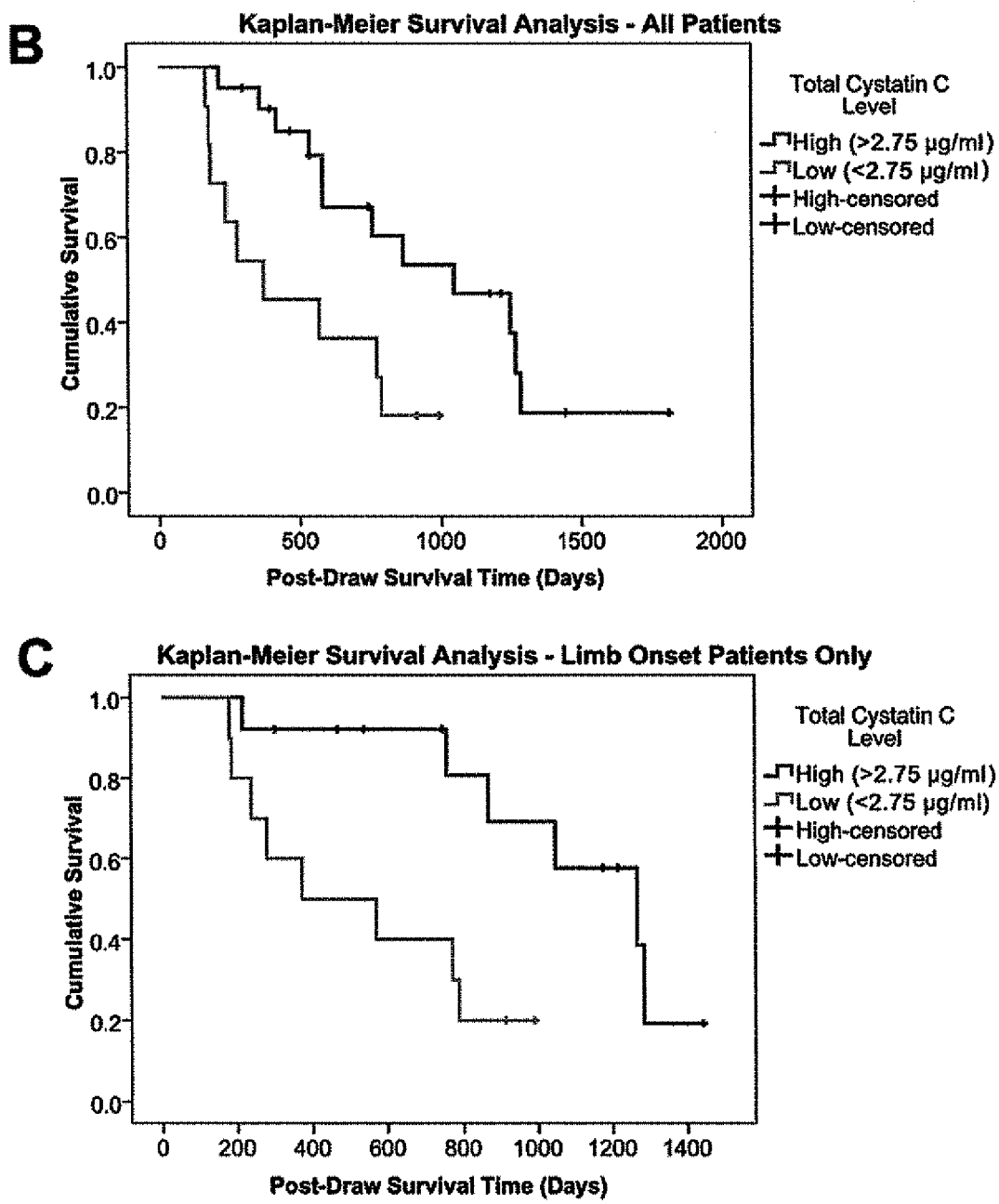
Figures 6B and C

Figures 12A-B

| | |
|---|---:|
| Kruskal-Wallis test | |
| P value | 0.0221 |
| Exact or approximate P value? | Gaussian Approximation |
| P value summary | * |
| Do the medians vary signif. (P < 0.05) | Yes |
| Number of groups | 4 |
| | |
| ALS vs HC | |
| Mann Whitney test | |
| P value | 0.0073 |
| | |
| ALS vs DC | |
| Mann Whitney test | |
| P value | 0.1298 |
| | |
| ALS vs Disease Mimics | |
| Mann Whitney test | |
| P value | 0.0626 |

Figures 15A-D
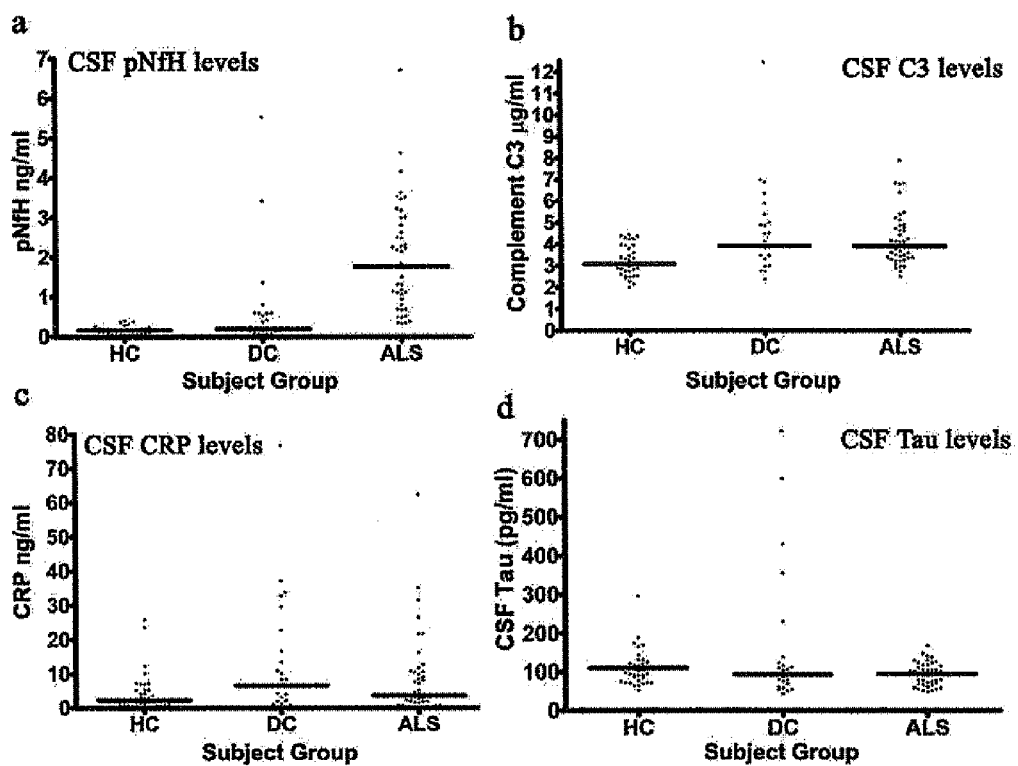

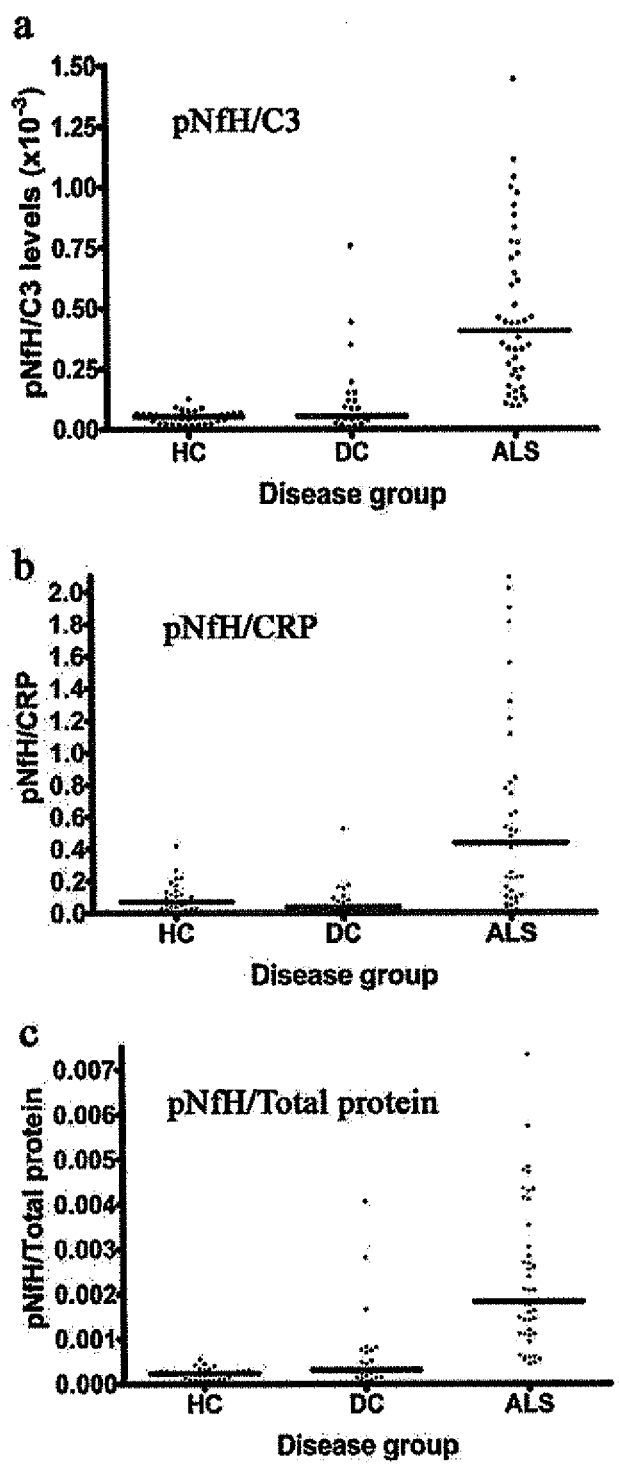
Figures 16A-C

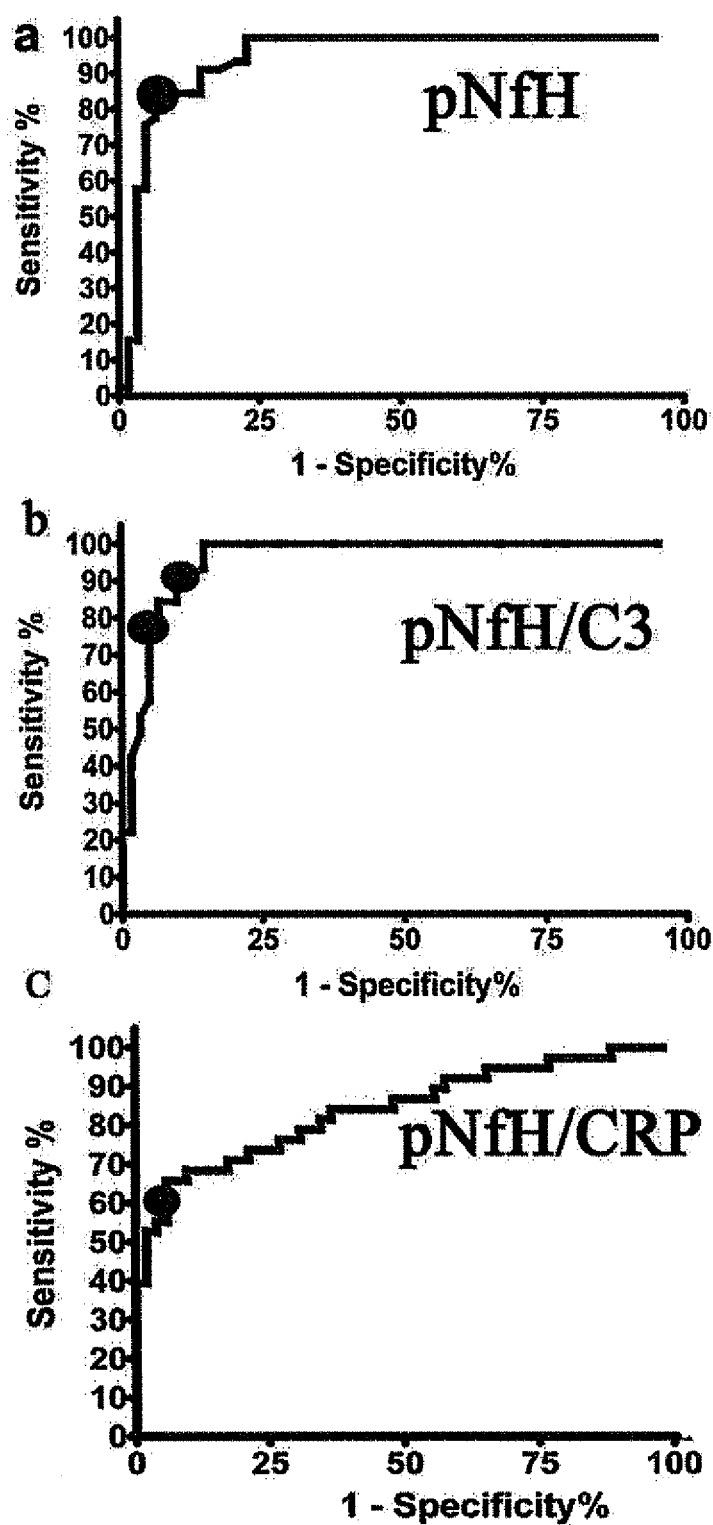
Figures 17A-C

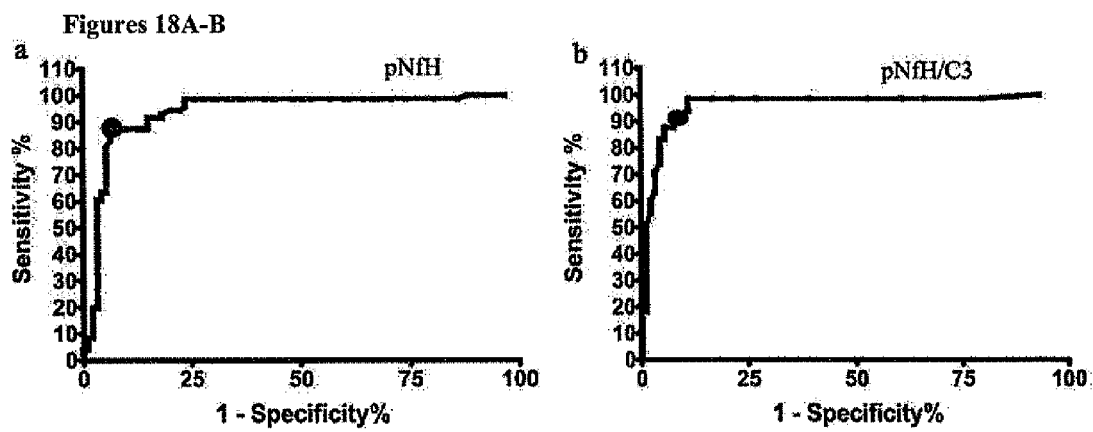
Figures 18A-B
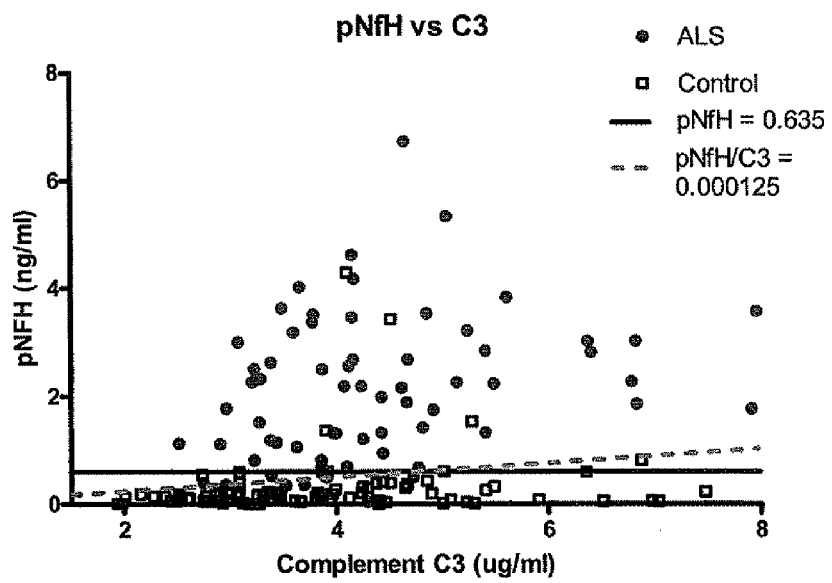
Figure 19

Figure 21A-B
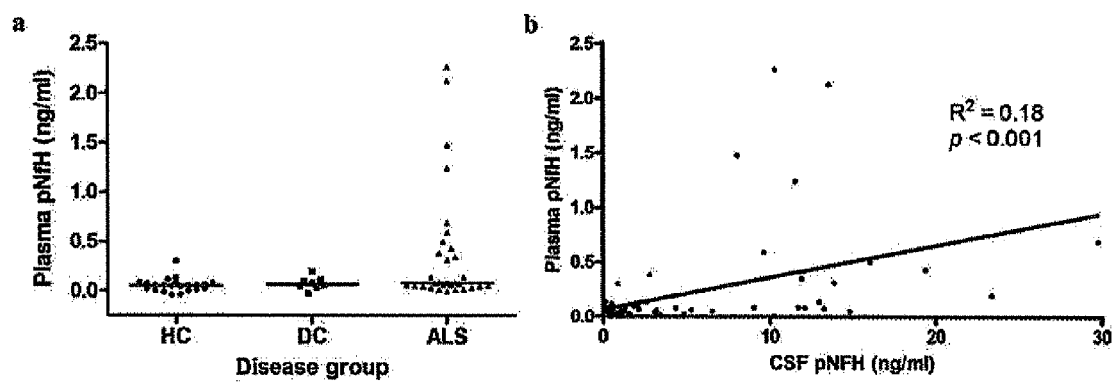

BIOMARKERS FOR THE DIAGNOSIS OF ALS

CROSS REFERENCE TO RELATED APPLICATIONS

This application claims the benefit of and priority to U.S. Provisional Patent Application No. 61/249,083, filed on Oct. 9, 2006, and U.S. Provisional Patent Application No. 61/311,144, filed on Mar. 5, 2010, the contents of each being incorporated by reference in their entirety.

STATEMENT REGARDING FEDERALLY SPONSORED RESEARCH OR DEVELOPMENT

This invention was made with Government Support under Agreement ES013469 award to Robert Bowser by the National Institutes of Health. The Government has certain rights in the invention.

FIELD OF THE INVENTION

The invention is generally related to biomarkers for amyotrophic lateral sclerosis and biomarkers correlated to patient survivability from limb onset amyotrophic lateral sclerosis.

BACKGROUND OF THE INVENTION

Amyotrophic lateral sclerosis (ALS), also known as Lou Gehrig's disease or motor neuron disease (MND), is one of several neurodegenerative diseases of the central nervous system. ALS is the most common adult onset motor neuron disease, affecting one in every 20,000 individuals, with an average age of onset of 50-55 years. ALS is characterized by rapidly progressive degeneration of motor neurons in the brain, brainstem, and spinal cord (Cleveland et al., *Nat. Rev. Neurosci.*, 2:806-19 (2001)). The median survival of patients from time of diagnosis is five years.

ALS exists in both sporadic and familial forms. Only 5-10% of all ALS cases are Familial ALS (FALS). Over the last decade, a number of basic and clinical research studies have focused on understanding the familial form of the disease, which has led to the identification of eight genetic mutations related to FALS. Transgenic mice expressing point mutants of the Cu/Zn superoxide dismutase-1 (SOD1) gene develop an age-dependent progressive motor weakness similar to human ALS due to a toxic gain of function (Rosen et al., *Nature*, 362:59-62 (1993); Rosen et al., *Hum Mol Genet*, 3, 981-987 (1994)).

These genetic mutations, however, do not explain sporadic ALS (SALS). The pathogenesis of SALS is multifactorial. A number of different model systems, including SOD1 transgenic mice, in vitro primary motor neuron cultures or spinal cord slice cultures, in vivo imaging studies, and postmortem examination of tissue samples, have been utilized to understand the pathogenesis of ALS (Subramaniam et al., *Nat. Neurosci.*, 5:301-307 (2002)). Although these studies have yielded therapeutic targets and several clinical trials, there are no drugs that delay disease onset or prolong long-term survival of ALS patients. Riluzole (Rilutek®, Aventis), a glutamate antagonist, currently is the only FDA-approved medication available to treat ALS. Riluzole, however, extends life expectancy by only a few months (Miller et al., Amyotrophic Lateral Sclerosis & Other Motor Neuron Disorders, 4, 191-206 (2003).). Creatine and a-tocopherol have shown some efficacy in relieving the symptoms of ALS in SOD1 transgenic mice, but exhibit minimal efficacy in human ALS patients (Groeneveld et al., *Annals of Neurology*, 53:437-45 (2003).

Studies have been performed which have identified early protein biomarkers for ALS, using mass spectrometry based proteomics of cerebrospinal fluid (CSF) and spinal cord samples of human subjects. For example, three neuroendocrine proteins (transthyretin, 7B2, and cystatin C) that exhibit alterations early in the disease pathogenesis in humans were identified in a proteomics analysis (US 20060178306 to Bowser).

Cystatin C has been identified using mass spectrometry as a diagnostic biomarker for ALS. CSF and lumbar spinal cord tissue samples from ALS subjects exhibit less cystatin C than control subjects. Cystatin C is a secreted protein that functions both as a cysteine protease inhibitor and can function as an autocrine or paracrine factor in neurogenesis of neural stem cells. Mutations in the cystatin C gene cause a rare disease called hereditary brain amyloid angiopathy, and increased levels of cystatin C have been found in other neurodegenerative diseases including Alzheimer's disease, ischemia, and Creutzfeldt-Jakob disease (CJD). Decreased levels of cystatin C in the CSF of ALS subjects or altered post-translational modifications to cystatin C suggest decreased levels of protease inhibitors, which may contribute to disease pathogenesis.

Despite the identification of early protein biomarkers for ALS, there remains a need, however, for improved methods for identifying therapeutic targets of ALS, and improved methods of diagnosing and monitoring the progress of the disease.

Therefore, it is an object of the invention to provide methods for diagnosing and monitoring ALS.

It is still another object to provide biomarkers for monitoring the progression of ALS.

It is another embodiment to provide methods and compositions for identifying agents for the treatment of ALS.

SUMMARY OF THE INVENTION

Methods for determining the onset of ALS in a subject are provided. One method includes analyzing a sample obtained from the subject for the presence or amount of one or more biomarkers indicative of ALS. In a preferred embodiment, the biomarkers are one or more of the following: C-reactive protein (CRP), cystatin c, plasminogen, complement C3, complement Factor H, CysGly-transthyretin, and phosphorylated neurofilament heavy chain (pNFH). The sample is typically cerebral spinal fluid (CSF) or blood. The levels or concentrations of the biomarkers can be used to determine the onset of ALS, monitor the progression of ALS, or monitor the progression of a treatment for ALS.

It has been discovered that in female subjects, pNFH levels or concentrations of $\geq 1.366$ ng/ml are indicative of ALS. In male subjects, complement C3 levels $\geq 1.197$ µg/ml and pNFH levels $\geq 1.366$ ng/ml are indicative of ALS. In male or female subjects, pNFH levels $\leq 0.645$ ng/ml indicate the subject is a healthy control. In female subjects, a complement C3 level between 1.005-4.475 µg/ml with a pNFH level between 0.645-1.366 ng/ml is indicative of ALS. If total CSF protein concentration is between 569-714 µg and pNFH is $\geq 1.366$ ng/ml, the subject has ALS. If total CSF protein concentration is $\geq 719$ µg/ml, complement C3 is between 1.005-4.475 µg/ml, and pNFH level is $\leq 0.645$ ng/ml, the subject is a healthy control. If complement C3 level is between 1.005-4.475 µg/ml and pNFH level is $\geq 1.366$ ng/ml, the subject has ALS. If complement C3 level is $\geq 4.475$ µg/ml and pNFH is ≦0.645 ng/ml then the subject is disease control. A disease control is a subject that has a neurological disease or condition other than ALS. Finally, if cystatin C level is ≦2.0 µg/ml and pNFH level is ≧0.75 ng/ml, the subject has ALS.

It has also been discovered that cystatin C levels in cerebrospinal fluid can be used to assess survivability of subjects having limb onset sporadic ALS. Thus, one embodiment provides a method for assessing survivability of an ALS subject comprising quantifying the levels of cystatin C in a sample obtained from the ALS subject wherein increased levels of cystatin C in the sample is indicative of increased survivability compared to ALS subjects having lower levels of cystatin C, wherein the ALS is limb onset ALS. It was also discovered that short survival times were most strongly associated with the lowest cystatin C levels, and identified a cut-off value of 2.75 µg/ml. Thus, one embodiment provides a method of determining survivability in a subject having ALS by determining the concentration of cystatin C in a sample obtained from the subject, wherein a concentration of cystatin C lower than 2.75 µg/ml indicates a decreased survivability compared to ALS subjects having greater than 2.75 µg/ml of cystatin in cerebrospinal fluid.

It has also been discovered that the ratio of pNFH to C3 levels can be used as a biomarker for assisting in the diagnoses of ALS. One embodiment provides a combination of the pNFH level and the pNFH/C3 ratio that provided 87.3% sensitivity and 94.6% specificity for ALS. In addition, the pNFH level correlated with overall patient survival. Increased plasma pNFH was detected in a subset of ALS patients and correlation of CSF and plasma pNFH levels within the same subject. CSF levels of pNFH and C3 assist in the diagnosis of ALS.

BRIEF DESCRIPTION OF THE DRAWINGS

FIG. 6B is Kaplan-Meier Survival Analysis of cumulative survival versus post-draw survival times between patients with greater than 2.75 µg/ml cystatin C (dark line) and patients with less than 2.75 µg/ml cystatin (grey line). FIG. 6C is Kaplan-Meier Survival Analysis of cumulative survival versus post-draw survival times between limb onset patients with greater than 2.75 µg/ml cystatin C (dark line) and patients with less than 2.75 µg/ml cystatin (grey line).

FIG. 12A is plot of the pNFH/C3 in patient populations. HC=healthy controls; DC=Disease controls; ALS=ALS patients. Each dot represents an individual subject. Horizontal line represents the median. Between ALS and healthy controls, pNfH/C3 levels were significantly different between ALS and healthy controls (Dunn's post-hoc test p<0.001, difference in rank sums=53.1). FIG. 12B is a graph of Receptor Operator Characteristic (ROC) curves generated for the pNFH/C3 ratio, with an area under the curve (AUROC)=0.9581 comparing ALS versus Controls to determine a threshold to achieve an optimum sensitivity and specificity as denoted by black circles. The optimal pNFH/C3 ratio was 0.125 and provided a sensitivity of 93.0% and specificity of 89.2% for 163 test subjects.

FIGS. 15A-D shows scatter plots for four candidate biomarkers. (A) pNFH (ng/ml), (B) Complement C3 (µg/ml), (C) C reactive protein (ng/ml) and (D) Total tau (pg/ml) were measured in the cerebrospinal fluid. (A) pNFH was significantly elevated in ALS compared to healthy and disease controls. (B) C3 was also significantly increased in ALS compared to healthy controls but not disease controls There were no significant alterations ($p>0.05$) across the subject groups for (C) CRP or (D) Tau. Horizontal line represents the median. HC: Healthy controls; DC: Disease controls; ALS: Amyotrophic lateral sclerosis. All statistical tests was deemed significant ($p<0.05$) using a One-way ANOVA with Dunn's multiple comparison test.

FIGS. 16A-C show scatter plots of the ratios for (A) pNFH/C3 (B) pNFH/CRP and (C) pNFH/Total protein. All scatter plots exhibited significant differences between ALS and the other control groups ($p<0.05$) using a One-way ANOVA with Dunn's multiple comparison test. Horizontal line represents the median. HC: Healthy controls, DC: Disease controls, ALS: Amyotrophic lateral sclerosis.

FIGS. 17A-C show ROC curves generated for (A) pNFH, AUROC=0.9401 (B) pNFH/C3, AUROC=0.9581 and (C) pNFH/CRP, AUROC=0.8406 comparing ALS versus Controls to determine a threshold to achieve an optimum sensitivity and specificity as denoted by black circles in each panel.

FIGS. 18A-B show ROC curves for (A) pNFH and (B) pNFH/C3 using the combined dataset to determine the final optimum thresholds (denoted by black circles) for sensitivity and specificity used in subsequent validation experiments. For pNFH>0.635 ng/ml, a sensitivity of 87.7% and specificity of 93.7% is achieved. For pNFH/C3>0.000125, a sensitivity of 87.7% and specificity of 94.6% is achieved.

FIG. 19 shows a two dimensional scatter plot comparing pNFH levels (ng/ml) versus C3 levels (µg/ml) in the CSF of each subject. Most control subjects with high levels of C3 exhibit low levels of pNFH. The lines illustrate the thresholds cut-off values generated from the ROC curves in FIG. 17. Increased sensitivity for ALS is generated by ALS cases that lie below pNFH=0.635 but above the pNFH/C3=0.000125 line.

FIG. 21A shows a scatter plot of plasma pNFH levels (ng/ml) for each subject groups. There was significant increase in plasma pNFH ($p<0.05$) as determined by one-way ANOVA with Dunn's multiple comparison test. FIG. 21B shows a scatter plot comparing plasma and CSF pNFH levels for each subject demonstrate correlation. Spearman's rank test ($R^2=0.18$, $p<0.001$).

DETAILED DESCRIPTION OF THE INVENTION

I. Definitions

Figure 1:
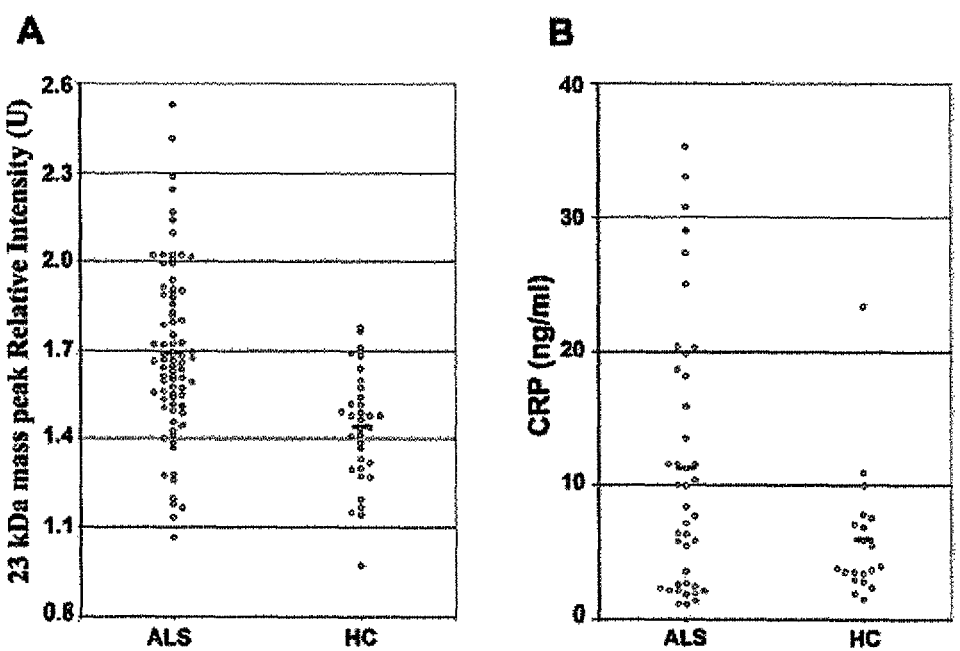
FIG. 1A is a graph of SELDI-TOF-MS relative intensity values of the 23.03 kDa peak for the 85 sporadic amyotrophic lateral sclerosis (SALS) and 41 healthy control subjects (HC) CSF samples.
FIG. 1B is a graph of C-reactive protein absolute concentration values (ng/mL) measured by ELISA using 41 SALS and 20 age-matched HC samples. A line in each subject group denotes the mean value.

The term "sample", as used herein refers to biological material isolated from an animal. The sample can contain any suitable biological material, but preferably comprises cells obtained from a particular tissue or biological fluid. The sample can be isolated from any suitable tissue or biological fluid. In this respect, the sample can be blood, blood serum, plasma, urine, or spinal cord tissue. In that ALS affects the central nervous system, the sample preferably is isolated from tissue or biological fluid of the central nervous system (CNS) (i.e., brain and spinal cord). In a preferred embodiment, the sample is isolated from cerebrospinal fluid (CSF).

The sample can be obtained in any suitable manner known in the art, such as, for example, by biopsy, blood sampling, urine sampling, lumbar puncture (i.e., spinal tap), ventricular puncture, and cisternal puncture. In a preferred embodiment, the sample is obtained by lumbar puncture, which also is referred to as a spinal tap or CSF collection. Lumbar puncture involves insertion of a spinal needle, usually between the 3rd and 4th lumbar vertebrae, into the subarachnoid space where CSF is collected. In instances where there is lumbar deformity or infection which would make lumbar puncture impossible or unreliable, the sample can be collected by ventricular puncture or cisternal puncture. Ventricular puncture typically is performed in human subjects with possible impending brain herniation. Ventricular puncture involves drilling a hole in the skull and inserting a needle directly into the lateral ventricle of the brain to collect CSF. Cisternal puncture involves insertion of a needle below the occipital bone (back of the skull), and can be hazardous due to the proximity of the needle to the brain stem. Many neurodegenerative diseases, such as Alzheimer's disease, Parkinson's disease, Huntington's disease, and ALS are characterized by the accumulation or presence of protein abnormalities which contribute to the disease phenotype. In addition to proteins, metabolite abnormalities in the sample can be used as an indicator of a diseased state.

The terms "individual", "host", "subject", and "patient" are used interchangeably herein, and refer to a mammal, including, but not limited to, humans, rodents such as mice and rats, and other laboratory animals.

The term "biomarker" refers to an organic molecule produced by an organism that is indicative or correlative of a disease state. Biomarkers include, but are not limited to, protein, metabolites, post-translationally modified proteins, etc.

II. Methods for Diagnosing ALS

Methods for determining the onset of ALS in a subject are provided. One method includes analyzing a sample obtained from the subject for the presence or amount of one or more biomarkers indicative of ALS. In a preferred embodiment, the biomarkers are one or more of the following: C-reactive protein (CRP), cystatin c, plasminogen, complement C3, Cys-Gly-transthyretin, and phosphorylated neurofilament heavy chain (pNFH).

In female subjects, pNFH levels or concentrations of $\geq 1.366$ ng/ml are indicative of ALS.

In male subjects, complement C3 levels>1.197 µg/ml and pNFH levels$\geq 1.366$ ng/ml are indicative of ALS.

In male or female subjects, pNFH levels$\leq 0.645$ ng/ml indicate the subject is a healthy control.

In female subjects, a complement C3 level between 1.005-4.475 µg/ml with a pNFH level between 0.645-1.366 ng/ml is indicative of ALS.

If total CSF protein concentration is between 569-714 µg/ml and pNFH is $\geq 1.366$ ng/ml, the subject has ALS.

If total CSF protein concentration is $\geq 719$ µg/ml, complement C3 is between 1.005-4.475 µg/ml, and pNFH level is $\leq 0.645$ ng/ml, the subject is a healthy control.

If complement C3 level is between 1.005-4.475 µg/ml and pNFH level is $\geq 1.366$ ng/ml, the subject has ALS.

If complement C3 level is $\geq 4.475$ µg/ml and pNFH is $\leq 0.645$ ng/ml then the subject is disease control. A disease control is a subject that has a neurological disease or condition other than ALS.

If cystatin C level is $\leq 2.0$ µg/ml and pNFH level is $\geq 0.75$ ng/ml, the subject has ALS.

If pNFH level is >0.6349 ng/ml AND pNFH/C3 ratio is >0.125, the subject has ALS.

A. C-Reactive Protein

CRP is another biomarker for ALS. The 23,030 Da mass spectral peak exhibited the single best sensitivity and specificity for ALS and has been reported to be C-reactive protein (CRP), an acute-phase inflammatory protein (Kuhle, J., et al., *Eur J Neurol*, 16:771-774 (2009); McGeer, P. L., et al., *Parkinsonism Relat Disord*, 10 Suppl 1:S3-7 (2004)). A statistically significant increase of CRP in ALS subjects was observed when compared to HC or AD subjects but no significant difference to MS or other disease control subjects. These results were validated by ELISA (FIGS. 1A and 1B). CRP levels were 5.84±1.01 µg/L for controls and 11.24±1.52 µg/L for ALS subjects as measured by ELISA.

A recent study found increased blood levels of CRP in ALS patients that correlated to ALSFRS measurements (Mitchell, R. M., et al., *Neurology*, 72:14-19 (2009)). Together, these findings suggest that systemic inflammation occurs in ALS patients. Alterations in another acute-phase protein, transthyretin, was observed during ALS.

Little is known about the role of CRP in the central nervous system, but it is expressed by neurons (20) and has been observed in neurofibrillary tangles during AD (21). The mean levels of CRP in control CSF have been reported to be 3.2 to 8 µg/L (22, 23), values similar to those in this study. A 2-fold elevated CSF level of CRP in ALS suggests a chronic but low level activation of the immune system.

B. Cystatin C as a Biomarker for Survivability

Figure 4:
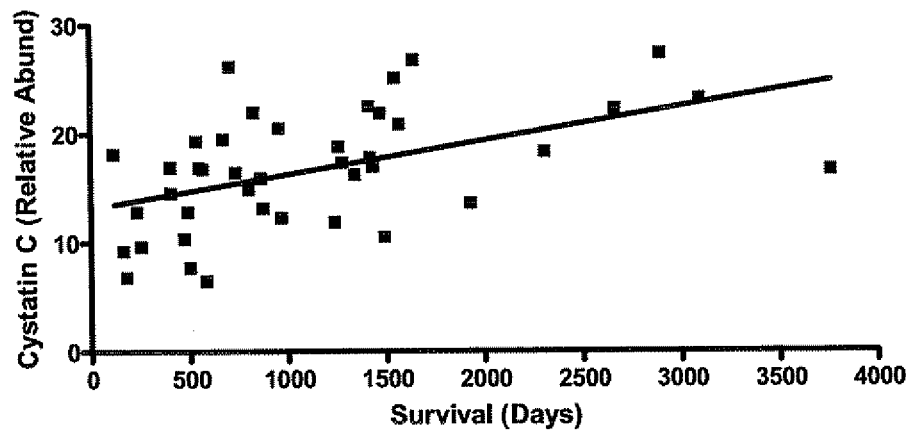
FIG. 4 is a line graph showing the correlation of the cystatin C mass peak from CFS (relative abundance) from limb onset ALS subjects to survival (days), defined as cystatin C (relative abundance) versus time from lumbar tap to patient death. Pearson correlation coefficient is r=0.486 (p=0.001).
Figure 5:
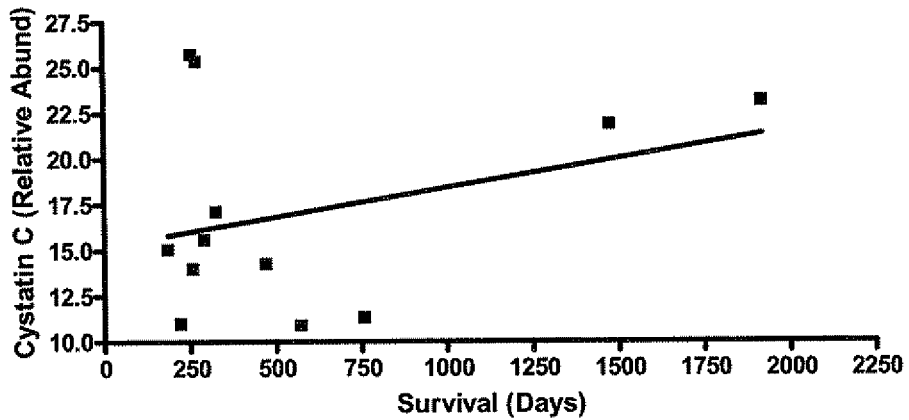
FIG. 5 is a line graph showing the correlation of the cystatin C mass peak intensity (relative abundance) from CFS from bulbar onset ALS subjects to survival (N=12), defined as the time from lumbar tap to bulbar onset patient death. Pearson correlation coefficient is r=0.3203 (p=0.31).
Figure 6A:
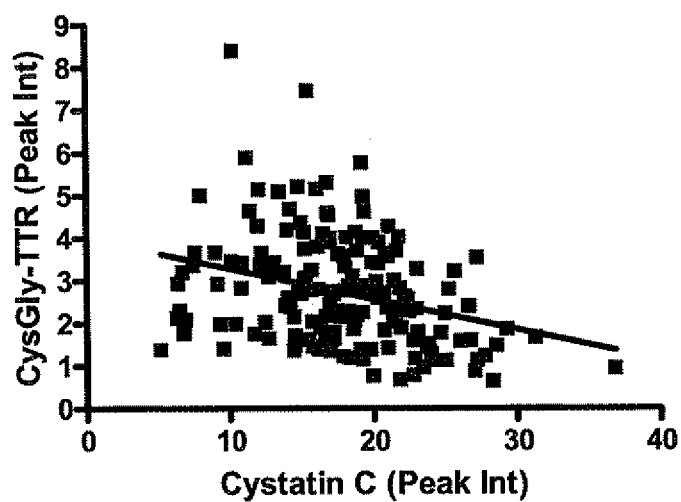
FIG. 6A is a line graph showing the correlation of the cystatin C mass peak intensity to the mass peak intensity for Cys-Gly-Transthyretin. Pearson correlation coefficient is r=−0.3073 (p<0.001).
Figure 7:
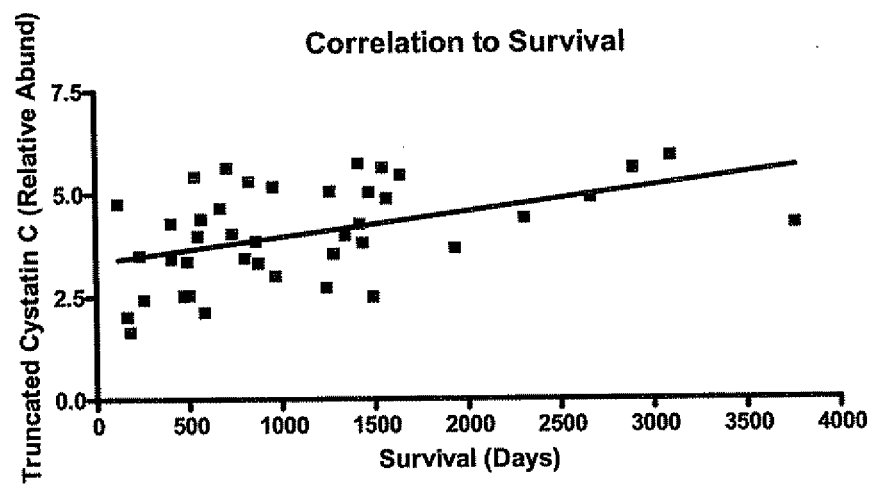
FIG. 7 is a line graph showing the correlation of a truncated cystatin C mass peak at 13.29 kDa (relative abundance) to survival (days) of limb onset ALS patients (N=41), defined as the time from lumbar tap to patient death. Pearson correlation coefficient is r=0.448 (p=0.0033).

Mass peak intensity values were correlated to patient survival. 50 of the SALS patients had survival information from date of lumbar tap to death. The level of cystatin C correlated to survival time for limb onset patients (FIG. 4). Cystatin C level did not correlate to survival in bulbar onset ALS patients (FIG. 5), and the levels of CRP or transthyretin did not correlate to patient survival in either limb or bulbar onset ALS patients (data not shown). The correlation between cystatin C to CysGly-transthyrein was also investigated (FIG. 6). Increased levels of CysGly-transthyrein correlated to lower levels of cystatin C in the same patient, thus indicating a correlation of oxidized forms of transthyretin to reduced cystatin C and shorter survival of the patient. The correlation of truncated cystatin C was also investigated (FIG. 7). Truncation of cystatin C occurs in vivo and can also occur upon long-term storage of CSF samples. Therefore we measured truncated cystatin C by mass spectrometry and determined the area under the curve for the truncated cystatin C mass peak and correlated that to survival in each patient. Our results demonstrate correlation of truncated cystatin C to ALS patient survival.

Thus, one embodiment provides a method for assessing survivability of an ALS subject comprising quantifying the levels of cystatin C (full-length or truncated) in a sample obtained from the ALS subject wherein increased levels of cystatin C in the sample is indicative of increased survivability compared to ALS subjects having lower levels of cystatin C.

C. Neurofilament Protein as a Biomarker for ALS

Levels of phosphorylated neurofilament heavy chain (pNFH) can be used to distinguish ALS from both disease and healthy controls with a sensitivity 87.7% and specificity of 93.7%. Additionally, the combination of pNFH and pNFH/C3 can be used to detect or diagnosis ALS with an overall sensitivity of 87.7% and a specificity of 94.6%. Survival data on 39 ALS cases demonstrated a moderate correlation between CSF pNFH levels and patient survival, showing pNFH as a prognostic marker.

A large number of disease control subjects were used covering a range of pathogenic conditions, including 14 ALS mimics that often are not easily distinguished based on clinical symptoms. The Examples show 12 of the 14 ALS mimics were distinguished from ALS using the rule combining pNFH and pNFH/C3. Two separate sets of CSF samples collected at two different medical centers using standardized sample collection and storage procedures.

Neurofilament heavy chain belongs to a family of intermediate filament proteins that form a major part of the neuronal cytoskeleton. Phosphorylated NFH is found in axons and is associated with slowing of neurofilament transport and expansion of the axonal caliber (Ackerley, S. et al., *J Cell Biol*, 161:489-495 (2003)). In ALS, however, phosphorylated neurofilament aggregates are seen within the perikaya and proximal axons of motor neurons. Furthermore, deletion/insertion mutations within the multiphosphorylation domain of NFH have been identified in approximately 1% of sporadic ALS cases (Al-Chalabi, A., et al., *Hum Mol Genet*, 8:157-164 (1999)). pNFH may be released into the interstitial fluid compartment during axonal injury/disintegration and accumulates in the CSF. Higher levels of pNFH were detected in the CSF of ALS patients versus other neurodegenerative diseases, including Alzheimer's disease, Parkinson's disease and FTD without motor involvement. The differences between neurodegenerative diseases may reflect the differences in the underlying neuronal cell type affected by each disorder. The axonal content of motor neurons is much larger than that of hippocampal pyramidal neurons or substantial nigral neurons and therefore the pNFH levels detected in the CSF upon neuronal injury or degeneration are reflective of this difference of total pNFH content between the neuronal subtypes. Consistent with this hypothesis, pNFH levels are highest in the spinal cord and brain stem when compared to various cortical and subcortical brain regions (Anderson, K. J., *J Neurotrauma*, 25:1079-1085 (2008)).

A statistically significant increase in plasma pNFH in ALS patients was observed compared to healthy control subjects, but not between ALS and disease control groups. There was a correlation between plasma and CSF levels, though absolute levels of pNFH detected in the blood are substantially less than that in the CSF. The lack of strong correlation suggests that pNFH accumulation in the blood may be limited by many factors, including degradation and dilution by the blood volume.

By incorporating C3 as a denominator, the ratio of pNFH/C3 effectively represents axonal degeneration versus CNS inflammation. This allows generation of a cut-off threshold providing greater sensitivity than pNFH alone with minimal loss of specificity.

There have been conflicting reports with regards to tau as a candidate biomarker for ALS (Paladin, P., et al. *Eur J Neurol*, 16:257-261 (2009); Sussmuth, S. D., et al., *Neurosci Lett*, 300:95-98 (2001)). No statistically significant alterations in total tau between ALS and controls were found. This is somewhat surprising since tau is also a cytoskeletal protein, though tau is also located in neuronal cell bodies and also in glia. It is plausible that the tau aggregation state or other interacting proteins affects measurements with the ELISA kit described in the Examples.

Cytoskeletal and inflammatory proteins were evaluated as candidate biomarkers to distinguish ALS from disease controls and healthy subjects. A rule combining pNFH and complement C3 levels was established and provided a sensitivity of 87.7% and specificity of 94.6% for detecting ALS. Combined with prior studies, the results confirm pNFH as a candidate biomarker for axonal degeneration and complement C3 as a biomarker for inflammation/innate immunity activation during ALS. C3 increases the specificity of the assay by incorporating inflammation within the variables that exist in ALS and other neurological disorders.

D. Neurofilament Protein as a Biomarker for Survivability

Figure 14:
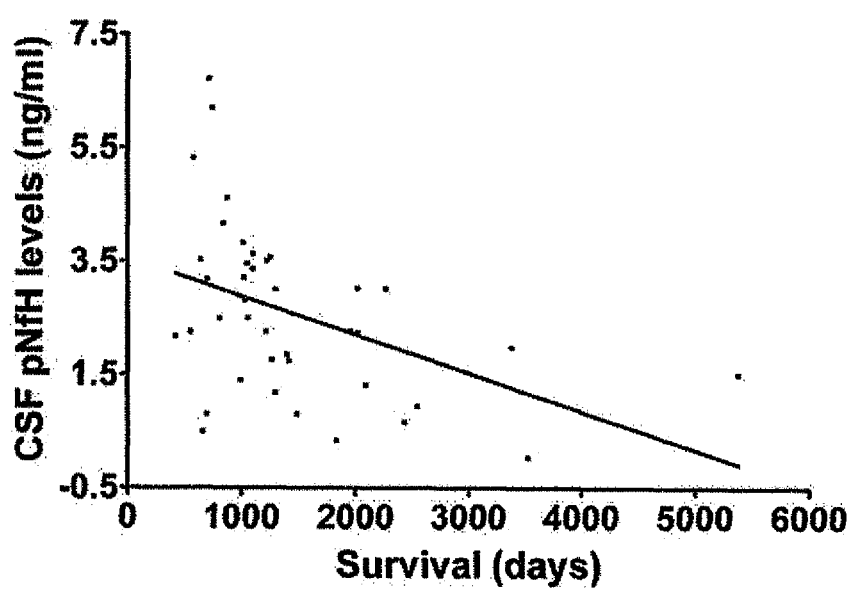
FIG. 14 is a line graph showing the correlation of a pNFH (ng/ml) detected by ELISA to survival (days) of limb onset ALS patients (N=41), defined as the time from lumbar tap to patient death. Spearman's rank correlation $R^2=-0.4638$, $p=0.0026$.

Phosphorylated neurofilament heavy chain (pNFH) levels measured by ELISA correlated to survival of limb onset ALS patients (FIG. 14). Therefore pNFH level is a biomarker for survival of limb onset ALS patients. Spearman's rank correlation $R^2=-0.4638$, $p=0.0026$.

E. Biomarker Panels

One embodiment provides biomarkers in cerebrospinal fluid for diagnosing ALS or for monitoring the treatment or progression of ALS. Representative biomarkers in CSF that are indicative of ALS are selected from the group consisting of m/z peak values of 3591, 6521, 6599, 6832, 6959, 7085, 7270, 15898, 19285, 19606, 21963, 23029. 25667, 26682, 26875, 27101, 27312, 42664, 5573, 7270, 9821, 10096, 13590, 19285, 21963, 25438, 25744, 5983, 7833, 7907, 8677, 10265, 11229, 11359, 11614, 11833, 12175, 12405, 14711, 14789 or a combination thereof.

Another embodiment provides a substrate having binding partners attached thereto, wherein the binding partners bind to one or more of C-reactive protein (CRP), cystatin c, plasminogen, complement C3, and phosphorylated neurofilament heavy chain (pNFH). A sample of CSF can be added to the substrate and biomarkers in the sample can be bound by the binding partners. A second binding partner with a detectable label can then be added to the substrate to detect any biomarkers bound to the substrate. Preferred binding partners include, but are not limited to antibodies and antigen binding fragments thereof.

III. Methods of Detecting Biomarkers for Amyotrophic Lateral Sclerosis

Preferred methods for detecting biomarkers for ALS in a sample include, but are not limited to immunohistological detection and mass spectroscopy.

A. Immunohistological Detection

In some embodiments, specific binding assays can be used for detecting the presence and/or measuring a level of the biomarker for ALS in a fluid sample, using binding reagents that specifically bind to the biomarkers to be detected. A binding reagent "specifically binds" to a biomarker when it binds with preferential or high affinity to the biomarker for which it is specific, but does not bind, does not substantially bind or binds with only low affinity to other substances.

The specific binding agent may be an antibody or antibody fragment specific for the ALS biomarker. The antibody may be a monoclonal or polyclonal antibody. Monoclonal antibodies are preferred. Antibodies also include antibody fragments, such as Fv, F(ab') and F(ab')$_2$ fragments as well as single chain antibodies. Suitable antibodies are available in the art. Antibodies and antibody fragments may also be generated using standard procedures known in the art. Aptamers and interacting fusion proteins may also be used as specific binding agents. Specific binding agents also include molecularly imprinted polymers (MIPs). MIPs, or "plastic antibodies", are polymers that are formed in the presence of a molecule that is extracted afterwards, thus leaving complementary cavities behind. The specific binding agent may recognize one or more form of the biomarker of interest.

Methods for using specific binding agents to detect biomarkers generally include the steps of:

a) contacting the sample with binding agents specific for a biomarker to be detected; and b) detecting binding between the binding agents and molecules of the sample.

Detection of specific binding of the antibody, when compared to a suitable control, is an indication that the metabolite being tested is present in the sample. Suitable controls include a sample known not to contain the biomarker, and a sample contacted with a binding agent (i.e., an antibody) not specific for the biomarker, e.g., an anti-idiotype antibody. A variety of methods to detect specific molecular interactions are known in the art and can be used in the method, including, but not limited to, immunoprecipitation, an enzyme immunoassay (i.e. an ELISA assay), and a radioimmunoassay. In general, the specific binding agent will be detectably labeled, either directly or indirectly. Direct labels include radioisotopes; enzymes whose products are detectable (e.g., luciferase, (3-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. The specific binding agent may be attached (coupled) to an insoluble support, such as a polystyrene plate or a bead. Indirect labels include secondary antibodies specific for metabolite-specific antibodies, wherein the secondary antibody is labeled as described above; and optionally contain members of specific binding pairs, e.g., biotin-avidin, etc. The biological sample may be brought into contact with and immobilized on a solid support or carrier. The support may then be washed with suitable buffers, followed by contacting with a detectably-labeled biomarker-specific binding agent.

B. Mass Spectrometry

Gas phase ion spectrometry requires a gas phase ion spectrometer to detect gas phase ions. Gas phase ion spectrometers include an ion source that supplies gas phase ions and include mass spectrometers, ion mobility spectrometers and total ion current measuring devices. Mass spectrometry (MS) is a preferred method for obtaining biomarker data. In one preferred embodiment, the disclosed biomarkers are detected using mass spectrometry methods.

A mass spectrometer is a gas phase ion spectrometer that measures a parameter which can be translated into mass-tocharge ratios (m/z) of gas phase ions. Mass spectrometers typically include an ion source and a mass analyzer. Examples of mass spectrometers are time-of-flight (ToF), magnetic sector, quadrupole filter, ion trap, ion cyclotron resonance, electrostatic sector analyzer and hybrids of these. A laser desorption mass spectrometer is a mass spectrometer which uses laser as a means to desorb, volatilize and ionize an analyte. A tandem mass spectrometer is mass spectrometer that is capable of performing two successive stages of m/z-based discrimination or separation of ions, including ions in an ion mixture. Methods for performing mass spectrometry on a sample are generally known in the art.

1. Liquid Chromatography-Mass Spectrometry (LC-MS)

Mass spectrometry can be combined with chromagraphic separation techniques to detect metabolites in complex mixtures such as serum or CSF. In one embodiment, biomarker are detected using liquid chromatography-mass spectrometry (LC-MS) which combines the physical separation capabilities of liquid chromatography with the mass analysis capabilities of mass spectrometry. Suitable mass analyzers for use in LC-MS include single quadrupole, triple quadrupole, ion trap, time-of-flight (TOF) and quadrupole-time-of-flight (Q-TOF). The TOF analyzer uses an electric field to give all ions the same kinetic energy, and then measures the time they take to reach the detector. If the particles all have the same charge, the kinetic energies are identical, and their velocities depend only on their masses with lighter ions reaching the detector first. In one embodiment, the metabolites are detected using LC-TOF mass spectrometry.

2. Direct Analysis in Real Time Mass Spectrometry (DART MS)

In some embodiments, the mass spectrometry method used to detect biomarkers of ALS does not include an initial chromatographic separation step. In a preferred embodiment, direct analysis in real time (DART) mass spectrometry is used. DART MS is a technique where a stream of excited metastables is used to desorb and chemically ionize a dried drop of solution containing analytes, such as a mixture of biomarkers extracted from CSF. A mass spectrometer is then used to evaluate the relative abundances of these biomarkers. The method displays no memory effects, as it is performed in a non-contact fashion. This increases the reproducibility of the biomarker fingerprints, enabling the detection of differences between disease states. Moreover, DART is able to ionize a broad range of material with varying polarities, enabling the simultaneous interrogation of multiple species.

IV. Systems for Detecting Biomarkers for ALS

Systems for detecting biomarkers for ALS are also provided. The systems can process a sample from a subject and analyze the sample for levels of one or more of the biomarkers disclosed herein, and apply one or more of the rules described in Table 4. Typically, the system includes a means for detecting or quantifying the biomarker, a computer, and an output means for reporting whether or not the subject has or is likely to develop ALS. The system can also be used for assessing the efficacy of a treatment for ALS. For example, one embodiment provides a method having the steps of administering a drug to a subject having ALS, and determining the levels of one or more biomarkers for ALS present in the sample wherein levels of pNFH<0.635 µg/ml and/or pNFH/C3≦0.000125 indicates the drug is effective at treating ALS.

Another embodiment provides a computer-implemented method of selecting a subject for treatment of amyotrophic lateral sclerosis (ALS) by inputting into a computer the concentration of pNFH and ratio of pNFH/C3 present in a sample from a subject suspected of having ALS and reporting that the subject has ALS when of pNFH<0.635 µg/ml and/or pNFH/ C3≦0.000125. The concentration data can be obtained by mass spectroscopy, immunochemistry, or ELISA assay data. The method can be used to assist in the diagnosis of ALS.

It will be appreciated that the computer-implemented method can use one or more of the rules in Table 4.

EXAMPLES

Example 1

Mass Spectrometry Identification of Biomarkers for ALS

Study Population

The study population comprised 85 sporadic ALS, 15 familial ALS, 18 multiple sclerosis (MS), 53 Alzheimer's disease (AD), 29 other neurologic disease (DC), and 41 healthy control (HC) subjects. All ALS patients fulfilled the E1 Escorial criteria for definite or probable ALS. For patient demographics see Supplemental Table 1. The DC group consisted of 7 neuropathy, 3 CNS metastasis, 2 pure lower motor neuron disease, 2 neuralgia, 2 demyelinating myelopathy, 2 frontal temporal dementia, 2 stroke, 1 normal pressure hydrocephalus, 1 superficial siderosis, 1 cerebral amyloid angiopathy, 1 Lyme disease, 1 viral encephalitis, 1 Parkinson's disease, 1 vertigo, 1 psychiatric patient with mental status change, and 1 conversion disorder patient. CSF samples (between 3-10 mL per subject) were obtained by lumbar puncture from 241 subjects. All samples were spun at 3000 rpm at 4° C. for 10 minutes to remove any cells and debris, aliquoted in small volumes and stored in low bind Eppendorf tubes at −80° C. within 2 hours from harvesting.

Cerebrospinal fluid samples were examined by Surface Enhanced Laser Dissociation/Ionization Time-of-Flight mass spectrometry (SELDI-TOF-MS). The mass peak with the best predictive value was validated by enzyme-linked immunosorbent assay (ELISA).

SELDI-TOF-MS and Spectra Analysis

For biomarker discovery 20 µL, CSF samples were incubated in 10 µL Urea/CHAPS buffer (9M urea, 2.5% CHAPS) for 10 minutes, mixed with 170 µL HEPES, pH 7.5 buffer. 150 µL of the sample was loaded onto HEPES buffer pre-equilibrated spots of Q10 Protein-Chips (Bio-Rad Laboratories, Hercules, Calif.) and incubated for 60 minutes to bind proteins to chip surface. Alternatively the CSF samples were loaded on Zn-IMAC30 Proteins-Chips (Bio-Rad Laboratories) by incubating 20 µL CSF in 10 µL Urea/CHAPS buffer for 10 minutes, mixed with 170 µL phosphate buffered saline (PBS), pH 7.4 for 60 minutes incubation on 100 mM Zinc sulfate pretreated IMAC30 Protein-Chips. Protein-Chips were rinsed with HPLC water 4-5 times, air dried and 50% saturated sinapinic acid (Sigma-Aldrich, St. Louis, Mo.) added to each spot.

Spectra were generated by focusing at three different mass ranges, each in duplicate. For the low mass range, 1,000 m/z to 10,000 m/z, we used a detector sensitivity of 8, intensity of 198 and a deflector setting of 250 Da. For mid mass range, 10,000 m/z to 20,000 m/z, detector sensitivity of 9, intensity of 198 and 500 Da deflector setting, and for high mass range, 20,000 m/z to 150,000 m/z, detector sensitivity of 10, intensity of 210 and 500 Da deflector setting. The ProteinChip Reader was calibrated prior to measurements.

The spectral data was subjected to baseline subtraction and normalized to total ion content. Spectra with a normalization coefficient either <0.33 or >3 were omitted to exclude artifacts. Peak detection was done at 1.5 signal to noise ratio (S/N), 1.5 valley depth and 20% min peak threshold. Ciphergen Biomarker Pattern Software version 3.0 (BPS) was used to identify peaks with high prediction values for ALS. Peaks with intensity value lower than 0.2 were removed prior to analysis.

The rule induction knowledge-based problem solving Rule Learner (RL) algorithm (12) was used in a 10-fold cross validation study on mass spectra (1.5-35 kDa mass range) from all CSF samples to generate a final set of predictive rules. 58,324 total mass peaks from the Q10 and Zn-IMAC30 protein chips were used in this analysis. Sensitivity, specificity and overall accuracy were generated from the 10-fold cross validation results. The results were compared to those we previously published (8) to evaluate the reproducibility across the separate studies.

To obtain putative protein identification of SELDI-TOF mass spectral peaks, we used the Empirical Proteomics Ontology Knowledge Base (http://www.dbmi.pitt.edu/EPO-KB).

C-Reactive Protein ELISA

C-reactive protein (CRP) concentrations in CSF were determined using a human CRP ELISA Kit (Millipore, item #CYT298) in accordance with the manufacturer's instructions. The CSF samples were diluted 1:10 in wash buffer for use in the assay. All ELISA measurements were performed in duplicate and each experiment repeated at least twice. The absorbance for each well was measured at 450 nm.

Statistics

For SELDI-TOF-MS data a significance level at $p<0.01$ was used. For all other data analysis we set a significance level of $p<0.05$. Data are expressed as mean±S.E.M. For group comparisons, Student's t-test and one-way ANOVA were used to determine statistical significance. For comparison of individual mass peaks across groups we used non-parametric Kruskal-Wallis ANOVA, followed by the Mann-Whitney U-test for pair wise comparisons. Pearson's test was used for testing correlation.

Results

After normalization, alignment and clustering of the spectra, 187 unique peaks above the chosen threshold could be detected in the IMAC dataset and 179 unique peaks in the Q10 dataset. Using a cut-off level of $p<0.01$, a total of 68 mass peaks were statistically significant between the SALS and HC groups, with 42 mass spectral peaks from the IMAC dataset and 26 from the Q10 dataset. Comparison of FALS to HC revealed 25 peaks in the IMAC dataset and 6 peaks in the Q10 dataset that were statistically significant, but comparing SALS and FALS yielded no statistically significant peak differences at $p<0.01$, and only a total of 8 mass peak differences at $p<0.05$ level. SALS versus DC revealed 27 statistically significant mass peaks, SALS versus MS generated 8 differently expressed peaks in the IMAC dataset and 3 in the Q10 dataset, and SALS versus AD resulted in 30 differently expressed peaks for IMAC and 5 for Q10 datasets. Database search using the Empirical Proteomics Ontology Knowledge Base (13) suggested possible protein identity for many mass peaks.

Example 2

Biomarker Peaks that Predict ALS from Control Subjects

A univariate statistical analysis of the SELDI-TOF-MS mass peaks was performed across all subject groups to identify biomarker mass peaks that distinguish subject groups with high predictive value. Initially sporadic ALS (SALS) was compared to healthy control (HC) subjects. The mass peak with the highest predictive value for separating SALS from HC subjects was a Q10 mass peak at 23,030 Da, with an overall accuracy of 69% (sensitivity of 65% and specificity of 79%) using a cut-off peak intensity value of 1.59 (FIG. 1A). A SELDI mass peak of this size was previously shown to be C-reactive protein (CRP) (14, 15). These findings were validated for CRP using a commercial CRP ELISA and CSF from 41 SALS 20 age-matched HC subjects (FIG. 1B). The CRP protein levels were 5.84±1.01 ng/mL for controls and 11.24±1.52 ng/mL for the ALS group (p=0.02). In the HC group there was a tendency (p=0.08) for increased CRP levels in the females (7.74±1.77 ng/mL, n=11) versus the males (3.51±0.62 ng/mL, n=9). Within the ALS group there was a non-significant (p=0.06) difference between patients with bulbar disease onset (19.69±5.78 ng/mL (n=6)) versus limb disease onset (10.64±1.73 ng/mL (n=34)). The CRP level in 6 FALS patients (9.91±2.34 ng/mL) was not significantly different to the SALS group. CRP ELISA results provided an overall accuracy of 62% (sensitivity of 51% and specificity of 85%) to discriminate ALS from HC using a cut-off value of 9 ng/mL.

Figure 2:
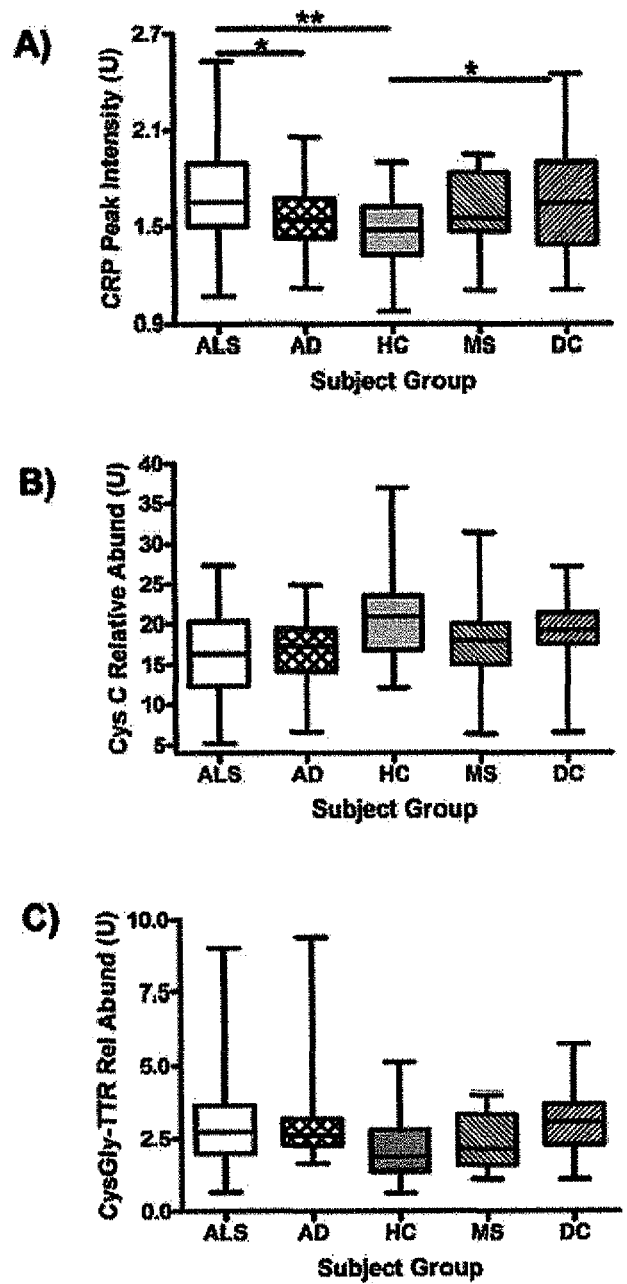
FIG. 2A is a box plot of CRP levels in sporadic amyotrophic lateral sclerosis (SALS), Alzheimer's Disease (AD), healthy control subjects (HC), multiple sclerosis (MS), and other neurologic disease (DC) subject groups as measured by SELDI-TOF-MS (Kruskal-Wallis test of the difference across all groups, p=0.002). The Mann-Whitney test for pair wise comparisons identified statistically significant CRP mass peak alterations between ALS and HC (**, p=0.002), ALS and AD (*, p=0.012), and DC and HC (*, p=0.014).
FIG. 2B is a box plot of cystatin C levels in all subject groups as measured by SELDI-TOF-MS (Kruskal-Wallis test of the difference across all groups, p=0.001). The ALS group is a combination of both the SALS and FALS subjects. Cystatin C peak intensity was significantly reduced in the ALS group when compared to the HC group (p=0.002) or to the DC group (p=0.01) as determined by the Mann Whitney U test. Cystatin C levels in the AD group were significantly decreased when compared to the HC group (p=0.004) or to the DC group (p=0.01).
FIG. 2C is a box plot of CysGly-transthyretin levels in all subject groups as measured by SELDI-TOF-MS (Kruskal-Wallis test of the difference across all groups, p=0.001). The ALS group is a combination of both the SALS and FALS subjects. Transthyretin peak intensity was significantly increased in the ALS group when compared to the HC group (p=0.002) or to the MS group (p=0.049) as determined by the Mann Whitney U test. Cys-Gly-transthyretin peak level in the AD group was also increased over that in the HC group (p=0.001). For all panels, the box represents the 25th to 75th quartile, with the horizontal bar representing the median and the whiskers the range.

The CRP mass peak provided an overall accuracy of 62% (sensitivity of 65% and specificity of 60%) for differentiating ALS from all non-ALS subjects. The drop in specificity across all groups was due to increased CRP levels in the CSF of DC and MS subject groups (FIG. 2A). The Mann-Whitney U-test for pair wise comparisons identified statistically significant CRP mass peak alterations between ALS and HC, ALS and AD, and DC and HC (FIG. 2A). There was no significant alteration in CRP levels between the ALS and MS or DC groups.

Both cystatin C and transthyretin were identified in prior mass spectrometry based proteomic studies as putative biomarkers for ALS (7, 8). In this study, the cystatin C peak at m/z 13,380 had an overall accuracy of 62% (sensitivity of 60% and specificity of 63%) for distinguishing ALS from the HC group, and an overall accuracy of 67% (sensitivity of 60% and specificity of 71%) for distinguishing ALS across all subject groups. The cystatin C mass peak exhibited statistically significant alterations between the ALS and HC groups, and the ALS and DC groups (FIG. 2B). This particular mass peak also was significantly reduced in AD subjects when compared to HC subjects (FIG. 2B).

Significantly reduced levels of native and double-charged transthyretin were found in SALS. Moreover, peaks at 6,959 Da and m/z 7,060 Da, which represent different conjugated species of transthyretin, were significantly increased in SALS. The 6,959 Da mass peak exhibited the best transthyretin predictive value with an accuracy of 65% (63% sensitivity and 70% specificity) for distinguishing ALS from the HC group, and an overall accuracy of 54% (sensitivity of 63% and specificity of 47%) for distinguishing ALS across all subject groups. This peak was described as the cysteinyl-glycine (CysGly) conjugated form of transthyretin. The 6,959 Da CysGly-transthyretin peak was significantly increased in ALS subjects when compared to the HC subject group (FIG. 2C). These results confirm prior SELDI-TOF-MS results for cystatin C and transthyretin alterations in ALS patients.

The 13,380 Da cystatin C mass peak exhibited 75% sensitivity and 84% specificity for distinguishing FALS from HC. Other proteins listed in Table 2 that exhibit significant alterations between the FALS and HC groups include neuroendocrine protein 7B2 we previously reported as a potential ALS biomarker, and chromogranin B that has been implicated in the secretion and toxicity of mutant SOD1.

Figure 3:
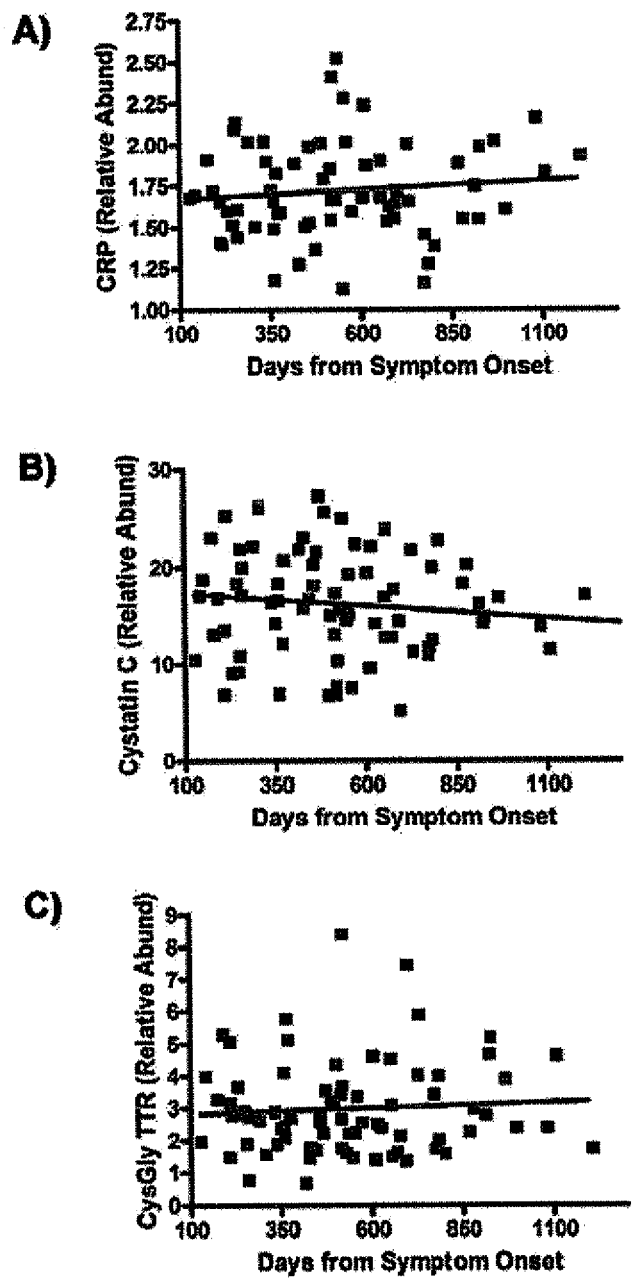
FIG. 3A is a line graph showing the correlation of the CRP (23,023 Da) mass peak (relative abundance) to ALS disease duration (days), defined as CRP relative abundance versus the time from clinical symptom onset to lumbar tap. Pearson correlation coefficient is r=0.096 (p=0.43).
FIG. 3B is a line graph showing cystatin C (13,377 Da) mass peak correlation to ALS disease duration, defined as cystatin C relative abundance versus the time from clinical symptom onset to lumbar tap. Pearson correlation coefficient is r=−0.208 (p=0.06).
FIG. 3C is a line graph showing CysGly-transthyretin (6,959 Da) mass peak correlation to ALS disease duration defined as CysGly-transthyetin relative abundance versus the time from clinical symptom onset to lumbar tap. Pearson correlation coefficient is r=0.058 (p=0.61).

The mass peak intensity values for CRP, cystatin C, and the 6,959 Da transthyretin peak were correlated to ALS disease duration for all SALS subjects (FIG. 3A-C). Disease duration was defined as the time from patient reported symptom onset to the lumbar tap. While there was a non-significant trend towards reduced cystatin C levels during disease duration (FIG. 3B), there was no correlation of CRP or transthyretin peak intensity levels to patient disease duration (FIGS. 3A and C).

Example 3

Biomarkers Correlated to Patient Survival

Mass peak intensity values were correlated to patient survival. 50 of the SALS patients had survival information from date of lumbar tap to death. The level of cystatin C correlated to survival time for limb onset patients (FIG. 4). Cystatin C level did not correlate to survival in bulbar onset ALS patients (FIG. 5), and the levels of CRP or transthyretin did not correlate to patient survival in either limb or bulbar onset ALS patients (data not shown). The correlation between cystatin C to CysGly-transthyrein was also investigated (FIG. 6). Increased levels of CysGly-transthyrein correlated to lower levels of cystatin C in the same patient, thus indicating a correlation of oxidized forms of transthyretin to reduced cystatin C and shorter survival of the patient. The correlation of truncated cystatin C was also investigated (FIG. 7). Truncation of cystatin C occurs in vivo and can also occur upon long-term storage of CSF samples. Therefore we measured truncated cystatin C by mass spectrometry and determined the area under the curve for the truncated cystatin C mass peak and correlated that to survival in each patient. Our results demonstrate correlation of truncated cystatin C to ALS patient survival.

The correlation of CSF cystatin C levels to ALS patient survival was explored by generating Kaplan-Meier survival curves for total CSF cystatin C measurements as measured by ELISA. For these analyses, patients were sorted into high- and low-cystatin C groups according to their first-draw cystatin C levels. Qualitative assessment revealed that short survival times were most strongly associated with the lowest cystatin C levels, and identified a cut-off value of 2.75 µg/ml that separated the ALS patients into a low cystatin C group (n=11) and a high cystatin C group (n=21). This analysis revealed significantly longer patient survival in the high cystatin C group than in the low cystatin C group (FIG. 6B). These statistical tests were repeated with exclusively limb-onset ALS patients. Within this population, the between-group difference in post-draw survival time became even more striking (FIG. 6C), further reinforcing Our finding that ALS patients with low CSF cystatin C levels exhibit reduced survival times relative to patients with average to high CSF cystatin C levels.

Example 4

Biomarker Panel for ALS

A multivariate analysis was performed to generate biomarker panels with predictive value for ALS using the Rule Learner (RL) algorithm. All CSF samples were used in a 10-fold cross validation study and the final biomarker panel predicted ALS with 82% overall accuracy (63% sensitivity, 94% specificity). A total of 41 mass peaks between 1.5-35 kDa were used by RL to generate the discriminatory rules (Table 1). The high level of specificity indicates the RL generated biomarker rules can readily distinguish non-ALS subjects. The lower level of sensitivity likely reflects ALS disease heterogeneity. Another indication of the overall sample heterogeneity is the large number of mass peaks used by RL to create discriminatory rules, reflecting the generation of rules that distinguish small sub-populations of samples. Three of the potential biomarker mass peaks listed in Table 1 are equivalent to those identified in a prior study that utilized only 54 CSF samples (8).

TABLE 1

| RL Biomarker Panel | |
|---|---|
| Protein Chip Array | m/z peak (kDa) |
| Q10 | 3.04, 3.07, 3.14, 3.22, 3.32, 3.41, 3.56, 3.59, 6.38, 13.73, 15.69, 27.49, 27.52, 27.63, 27.67, 27.68, 27.73, 27.86, 30.26 |
| Zn-IMAC | 5.24, 5.26, 5.74, 5.75, 5.77, 6.12, 6.13, 6.81, 11.71, 11.94, 17.14, 17.54, 17.56, 19.70, 20.50, 20.70, 20.71, 20.72, 20.73, 20.74, 31.53, 33.80 |

Example 5

ELISA Study to Identify Biomarkers for Motor Neuron Disease

For the ELISA, cerebrospinal fluid (CSF) from 108 subjects was used, including 45 ALS, 27 other neurologic disease controls, and 36 healthy controls. Proteins measured by ELISA were cystatin c, plasminogen, complement C3, C-reactive protein (CRP), phosphorylated neurofilament heavy chain (pNFH), and hemoglobin. Total protein content in each CSF sample was also measured, and the subjects age, gender, site of symptom onset, and diagnosis were noted.

This dataset was analyzed by multiple statistical approaches, including a clustering analysis using k-means clustering, Rule learner based algorithm, and the area under a receiver operating characteristic curve (AUROC).

The following rules were developed that differentiated ALS from the control groups:
1) If Gender is Female, and pNFH level is 1.366 ng/ml, then subject is ALS.
2) If Gender is Male, and complement C3 level is 1.197 µg/ml and pNFH level is $\geq$1.366 ng/ml, then subject is ALS.
3) If pNFH level is 0.645 ng/ml, then subject is healthy control.
4) If Gender is Female, and complement C3 level is between 1.005-4.475 µg/ml and pNFH is between 0.645-1.366 ng/ml, then subject is ALS.
5) If total CSF protein concentration is between 569-714 µg/ml and pNFH level is $\geq$1.366 ng/ml, then subject is ALS
6) If total CSF protein concentration is $\geq$719 µg/ml, complement C3 between 1.005-4.475 µg/ml and pNFH level is 0.645 ng/ml, then subject is healthy control
7) If complement C3 level is between 1.005-4.475 µg/ml and pNFH level is 1.366 ng/ml, then subject is ALS
8) If complement C3 level is $\geq$4.475 µg/ml and pNFH level is 0.645 ng/ml, then subject is disease control
9) If cystatin C level is 2.0 µg/ml and pNFH level is 0.75 ng/ml, then subject is ALS Using these rules and comparing ALS to all other subjects in the 108 sample set described above, an overall accuracy of 91% and AUROC of 0.88 was obtained. Comparing ALS to just healthy controls generated an overall accuracy of 95% and AUROC of 0.99. Comparing ALS to only the other neurological disease controls generated an overall accuracy of 85% and AUROC of 0.81.

In a separate analysis of 163 subjects, if pNFH level is >0.6349 ng/ml AND pNFH/C3 ratio is >0.125, then the subject has ALS. This rule of pNFH >0.6349 gn/ml AND pNFH/C3>0.125 gave a sensitivity of 87.3% and a specificity of 94.6%.

ELISA was also used to measure levels of complement Factor H. If Factor H is >2.16 ug/ml and subject is less than or equal to 47 years old, the subject has ALS. If Factor H is >3.035 ug/ml and subject is more than 47 years old, the subject has ALS.

Example 6

LC-MS/MS Analysis for Biomarkers for Neurological Disease

LC-MS/MS analysis was performed on over 200 CSF samples from various ALS and control subjects. Subjects were pooled into 25 groups, each controlled for type of disease, site of disease onset, current medications, age, and gender. Semi-quantitative data was obtained based on peptide counts per protein. Table 2 contains data on the assayed proteins.

| UniProt Acession | Protein | SALS G01 <40L | SALS G02 <40L | SALS G03 4060L | SALS G04 4060L R | SALS G05 4060L R | SALS G06 4060B | SALS G07 >60L | SALS G08 >60R | SALS G09 >60B |
|---|---|---|---|---|---|---|---|---|---|---|
| P01019 | Angiotensinogen precursor - *Homo sapiens* (Human) | 80 | 94 | 77 | 81 | 68 | 84 | 85 | 70 | 94 |
| P36955 | Pigment epithelium-derived factor precursor *Homo sapiens* (Human) | 86 | 75 | 73 | 76 | 64 | 70 | 62 | 63 | 66 |
| P01042 | Kininogen-1 precursor - *Homo sapiens* (Human) | 2 | | | 1 | 1 | 2 | | | |
| Q6JIA6 | Kallikrein 6 variant 4 - *Homo sapiens* (Human) | | | | | 1 | | | | |
| Q7KZ97 | Antithrombin III variant - *Homo sapiens* (Human) | 31 | 32 | 30 | 33 | 24 | 28 | 19 | 30 | 32 |
| P00747 | Plasminogen precursor - *Homo sapiens* (Human) | 16 | 10 | 11 | 12 | 12 | 12 | 7 | 10 | 10 |
| Q53F31 | Vitamin D-binding protein variant - *Homo sapiens* (Human) | 3 | 3 | 5 | 5 | 7 | 3 | 4 | 3 | 2 |
| Q16270 | Insulin-like growth factor-binding protein 7 precursor - *Homo sapiens* (Humans) | 12 | 12 | 10 | 11 | 11 | 14 | 11 | 8 | 11 |
| P24592 | Insulin-like growth factor-binding protein 6 precursor - *Homo sapiens* (Humans) | 6 | 10 | 9 | 8 | 12 | 8 | 12 | 8 | 8 |
| P01034 | Crystatin-C precursor - *Homo sapiens* (Human) | 172 | 192 | 151 | 156 | 145 | 174 | 172 | 155 | 177 |
| P05408 | Neuroendocrine protein 7B2 precursor - *Homo sapiens* (Human) | 5 | 5 | 5 | 4 | 5 | 5 | 3 | 2 | 2 |

| UniProt Acession | Protein | FALS G10 3060L | FALS G11 4087 | Norm G12 <40 | Norm G13 <40 | Norm G14 <40 | Norm G15 3060 | Norm G16 4060 | Norm G17 4060 | Norm G18 >60 | Norm G19 >60 |
|---|---|---|---|---|---|---|---|---|---|---|---|
| P01019 | Angiotensinogen preccursor - *Homo sapiens* (Human) | 82 | 74 | 92 | 82 | 77 | 92 | 88 | 90 | 103 | 90 |
| P36955 | Pigment epithelium-derivied factor precursor *Homo sapiens* (Human) | 67 | 75 | 72 | 71 | 61 | 67 | 70 | 72 | 70 | 71 |
| P01042 | Kininogen-1 precursor - *Homo sapiens* (Human) | | | | | 1 | 1 | | 1 | | 1 |
| Q6JIA6 | Kallikrein 6 variant 4 - *Homo sapiens* (Human) | | | | | | 1 | 1 | | | |
| Q7KZ97 | Antithrombin III variant - *Homo sapiens* (Human) | 27 | 26 | 20 | 16 | 23 | 23 | 22 | 27 | 20 | 15 |
| P00747 | Plasminogen precursor - *Homo sapiens* (Human) | 11 | 12 | 7 | 9 | 7 | 8 | 6 | 10 | 4 | 7 |
| Q53F31 | Vitamin D-binding protein variant - Homo *sapiens* (Human) | 2 | 4 | 4 | 3 | 4 | 3 | 2 | 4 | 4 | 3 |
| Q16270 | Insulin-like growth factor-binding protein 7 precursor - *Homo sapiens* (Humans) | 11 | 11 | 13 | 9 | 10 | 12 | 8 | 9 | 8 | 9 |
| P24592 | Insulin-like growth factor-binding protein 6 precursor - *Homo sapiens* (Humans) | 7 | 7 | 9 | 6 | 6 | 6 | 10 | 8 | 7 | 8 |
| P01034 | Crystatin-C precursor - *Homo sapiens* (Human) | 215 | 193 | 189 | 188 | 171 | 178 | 172 | 165 | 131 | 159 |
| P05408 | Neuroendocrine protein 7B2 precursor - *Homo sapiens* (Human) | 5 | 4 | 3 | 5 | 1 | 3 | 4 | 2 | | 2 |

| UniProt Acession | Protein | MS G20 <40 | MS G21 4070 | LMND G22 | UMND G23 | AlzD G24 <60 | AlzD G25 >60 | Reference |
|---|---|---|---|---|---|---|---|---|
| P01019 | Angiotensinogen preccursor - *Homo sapiens* (Human) | 77 | 78 | 80 | 87 | 75 | 77 | ANGT_HUMAN |

-continued

| | | | | | | | | |
|---|---|---|---|---|---|---|---|---|
| P36955 | Pigment epithelium-derivied factor precursor Homo sapiens (Human) | 61 | 68 | 52 | 64 | 65 | 70 | PEDF_HUMAN |
| P01042 | Kininogen-1 precursor - Homo sapiens (Human) | | 1 | | | | | KNG1_HUMAN |
| Q6JIA6 | Kallikrein 6 variant 4 - Homo sapiens (Human) | | | | | | | Q6JIA6_HUMAN |
| Q7KZ97 | Antithrombin III variant - Homo sapiens (Human) | 16 | 18 | 28 | 26 | 29 | 22 | Q7KZ97_HUMAN |
| P00747 | Plasminogen precursor - Homo sapiens (Human) | 8 | 9 | 8 | 3 | 6 | 6 | PLMN_HUMAN |
| Q53F31 | Vitamin D-binding protein variant - Homo sapiens (Human) | 4 | 3 | 4 | 3 | 1 | 2 | Q53F31_HUMAN |
| Q16270 | Insulin-like growth factor-binding protein 7 precursor - Homo sapiens (Humans) | 9 | 11 | 5 | 7 | 8 | 10 | IBP7_HUMAN |
| P24592 | Insulin-like growth factor-binding protein 6 precursor - Homo sapiens (Humans) | 7 | 9 | 9 | 9 | 6 | 7 | IBP6_HUMAN |
| P01034 | Crystatin-C precursor - Homo sapiens (Human) | 158 | 184 | 165 | 153 | 131 | 156 | CYTC_HUMAN |
| P05408 | Neuroendocrine protein 7B2 precursor - Homo sapiens (Human) | 2 | 3 | | 2 | | 1 | 7B2_HUMAN |

Figure 8:
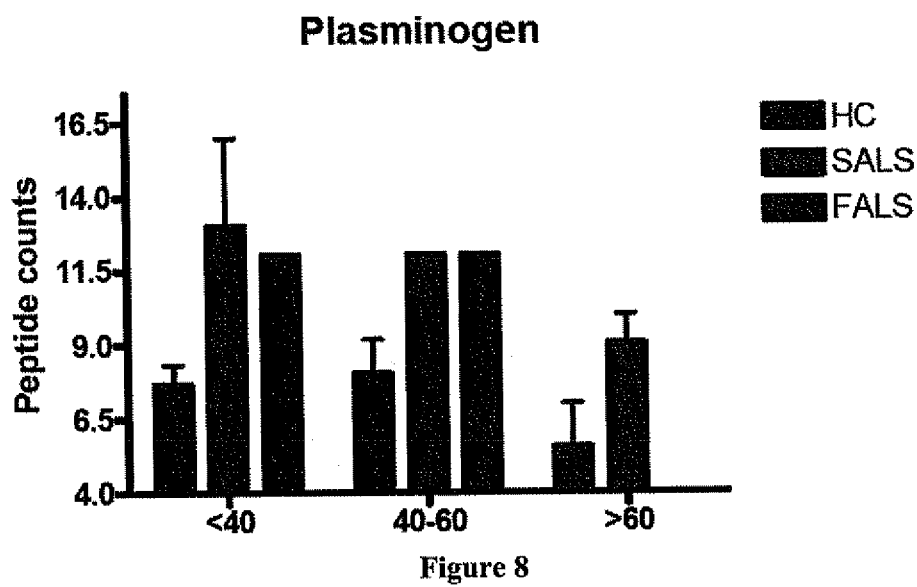
FIG. 8 shows a bar graph of plasminogen peptide counts in CSF taken from healthy control subjects (HC), sporadic amyotrophic lateral sclerosis (SALS), and familial amyotrophic lateral sclerosis (FALS) in age groups <40, 40-60, and >60.
Figure 9:
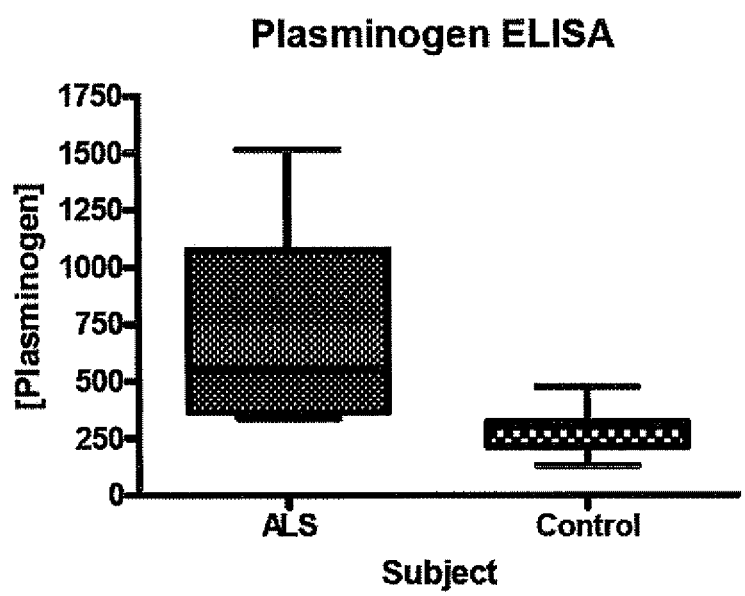
FIG. 9 shows a box plot of plasminogen concentration in CSF taken from subjects with ALS and normal healthy control subjects.
Figure 10:
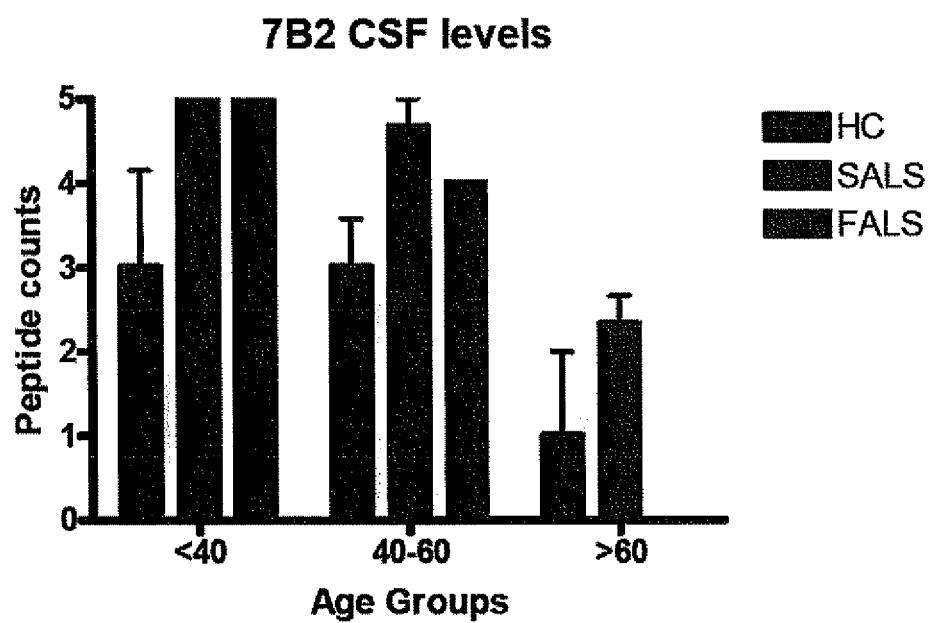
FIG. 10 shows a bar graph of neuroendocrine protein 7B2 peptide counts in CSF taken from healthy control subjects (HC), sporadic amyotrophic lateral sclerosis (SALS), and familial amyotrophic lateral sclerosis (FALS) in age groups <40, 40-60, and >60.
Figure 11:
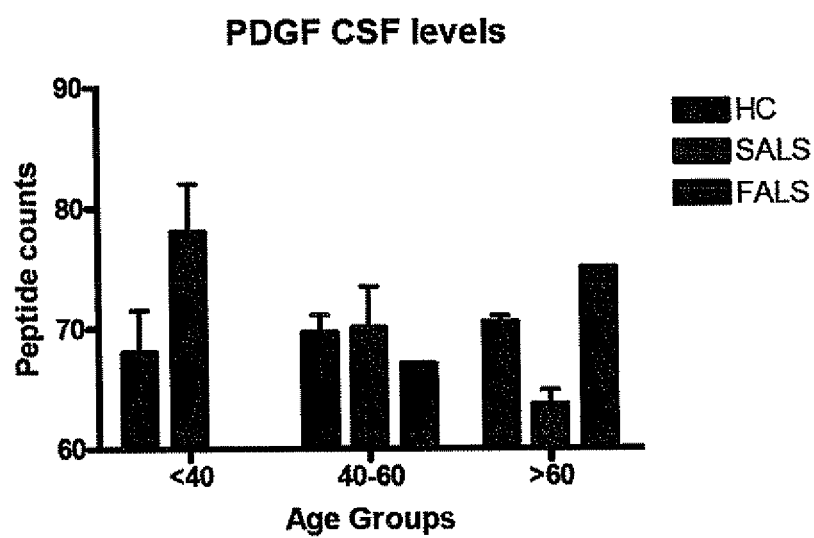
FIG. 11 is a bar graph of PDGF peptide counts in CSF taken from healthy control subjects (HC), sporadic amyotrophic lateral sclerosis (SALS), and familial amyotrophic lateral sclerosis (FALS) in age groups <40, 40-60, and >60.
Figure 12:
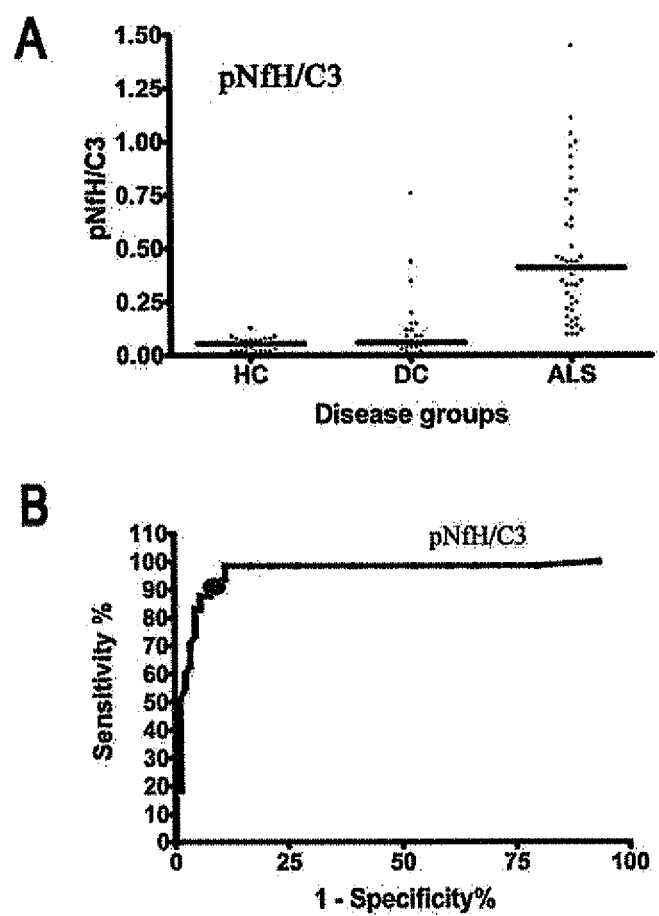
FIGS. 12A-B are a plots of the pNFH/C3 ratio in different patient populations and a ROC analysis for prediction of ALS.
Figure 13:
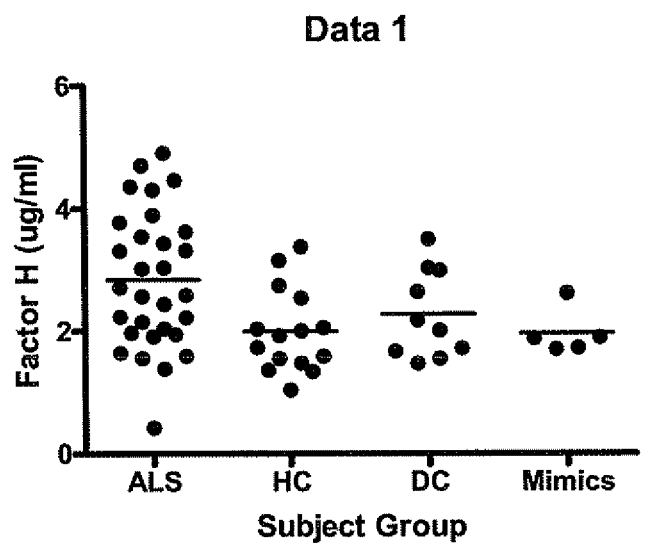
FIG. 13 is a plot of complement Factor H concentration (µg/ml) in CSF taken from subjects with ALS, healthy controls, neurologic disease controls without motor involvement, and disease mimics of ALS. Each dot represents an individual subject. Statistical analysis for group comparisons demonstrated significant alterations across all groups. Disease mimics included primary lateral sclerosis, pure lower motor neuron disease, small fiber neuropathy, and sensorimotor polyneuropathy. There were statistically significant differences between ALS and healthy controls and a trend towards significance between ALS and disease mimics.

There is an increase in plasminogen protein levels in the CSF of sporadic (SALS) and familial (FALS) forms of the disease determined using LC-MS/MS (FIG. 8) and ELISA (FIG. 9). 7B2 levels are also increased in ALS patients as measured by LC-MS/MS (FIG. 10). PDGF levels are increased in the CSF of ALS patients that are less than 40 years old (FIG. 11). No statistically significant change was observed in other age groups.

Example 7 pNFH is a Biomarker for ALS

Clinical Details and Sample Collection

Patients were recruited at either the University of Pittsburgh Medical Center (UPMC) or Massachusetts General Hospital (MGH) upon informed patient consent. The study was approved by both UPMC and MGH institutional review boards. All ALS subjects (n=71) were defined as possible, probable, probable laboratory-supported or definite ALS by El Escorial criteria by experienced neurologists specialized in motor neuron disease. The disease control (DC) group (n=52) comprised a range of diseases including: 14 ALS mimics (2 Primary lateral sclerosis, 4 Hereditary spastic paraplegia, 1 Progressive Muscular Atrophy, 1 Multifocal motor neuropathy with conduction block, 5 Peripheral neuropathy, 1 chronic inflammatory demyelinating polyneuropathy); 15 Multiple Sclerosis cases (one had co-existent lupus); 6 Neurodegenerative conditions (2 Frontotemporal lobe dementia without motor involvement, 2 Alzheimer's Disease, 1 Parkinson's disease, 1 Spinocerebellar ataxia); 4 Neoplasia cases (Lymphoma and secondary metastasis); 3 Inflammatory conditions (2 Myelopathy, 1 Neurosarcoidosis); 5 infectious diseases (1 Viral encephalitis, 2 Lyme's disease, 2 Aseptic meningitis); 2 Metabolic (Seizure disorder, Superficial siderosis); 1 Migraine; 1 Conversion disorder; and 1 Normal pressure hydrocephalus. The healthy control (HC) group (n=40) consisted of age-matched healthy volunteers from the community. The ethnicity was predominantly Caucasian with only four documented cases from minority ethnic groups.

A training set of 106 subjects from the UPMC clinic and a test set of 57 subjects from the MGH clinic were generated. The clinical details for each subject group are listed in Table 1.

All samples were processed and stored at −80° C. within 2 hours of collection. CSF was collected by lumbar puncture into polypropylene tubes and centrifuged at 450-g for 5 minutes at 4° C. to remove any cells and debris, aliquoted in small volumes and stored in low bind Eppendorf tubes at −80° C. Serum was collected at the same office visit into ethylenediaminetetracetic acid (EDTA) tubes, incubated for 30 minutes at room temperature, centrifuged at 1733-g for 10 minutes at 4° C. and the layer containing plasma removed and aliquoted in small volumes and stored in low bind Eppendorf tubes at −80° C.

ELISA

Total protein was determined using the BCA Protein Assay Kit (Thermo Scientific, Waltham, Mass.). Levels of candidate biomarkers measured in the CSF were determined using commercial ELISA kits to the Human C-Reactive Protein (CRP) (Millipore, Billerica, Mass.), human phosphorylated Neurofilament H (BioVendor Research and Diagnostic Products, Modrice, Czech Republic) and human total Tau (Invitrogen, Camarillo, Calif.). A separate commercial kit was used to determining plasma pNfH levels (EnCor Biotechnology Inc, Gainsville, Fla.). This ELISA kit has been previously described and shown to measure pNFH in human plasma [6] Samples were run in triplicate and each experiment repeated at least twice.

An ELISA was developed within the laboratory using commercially available antibodies to measure levels of C3 in cerebrospinal fluid. Costar 96 well EIA/RIA high binding plates (Corning, Inc. Cat No. 3590 were coated with 2 μg/ml Affi-Anti C3 IgY, (Genway, San Diego, Calif.), diluted in 0.05M Carbonate-Bicarbonate, pH 9.6 for 60 minutes at room temperature, 100 μl/well. The plates were then washed 3 times with 0.05% Tween 20 in PBS, pH 7.4 followed by incubation with 200 μl/well of blocking solution (Superblock T20 (PBS) Blocking Buffer, Thermo Scientific, Rockford, Ill.) for 60 minutes at room temperature. After washes, plates were incubated with 100 μl of the sample, diluted 1 in 50 with sample buffer (Superblock T20 (PBS) Blocking Buffer). A standard curve was generated using a human complement C3 Protein Standard, (Genway, San Diego, Calif.) diluted in blocking solution to 500 ng/ml followed by serial dilutions. Plates were incubated with 100 μl/well. Duplicates were run with a coefficient of variations within 10%. After washes, the plates were incubated 100 μl/well of 0.2 mg/ml Affi-anti C3 IgY-HRP (Genway, San Diego, Calif.) diluted in sample buffer for 60 minutes at room temperature. 100 µl/well of TMB Peroxidase Substrate System (KPL, Gaithersburgh, Md.) was used to visualize the reaction product and the absorbance values were read at 450 nm. Net absorbance was calculated by deducting the mean value obtained for a duplicate of "blank" wells containing diluent buffer only.

Statistics

For group comparisons, non-parametric t-test and one-way ANOVA were used to determine statistical significance. For comparison of individual mass peaks across three groups we used non-parametric Kruskal-Wallis ANOVA, followed by Dunn's multiple comparison test for pair wise group comparisons. For all data analysis we set a significance level of $p<0.05$. Spearman's rank test was used for non-parametric correlation analysis and Pearson test was performed for pair-wise correlation analysis for pNFH to patient survival. All statistical analysis was performed using GraphPad Prism 5.0 software.

Results

Levels of phosphorylated neurofilament heavy chain (pNFH), total tau (Tau), complement C3 (C3), and C-reactive protein (CRP) in the CSF of a training set consisting of 106 subjects (Table 1A) were measured. The median level of pNFH was 1.77 ng/ml, 0.2 ng/ml and 0.165 ng/ml for ALS, DC and HC respectively (FIG. 15a). This median level for ALS patients is similar to the mean value of 1.7 ng/ml reported earlier (Brettschneider, J., et al., Neurology, 66:852-856 (2006)). pNFH was significantly elevated in ALS compared to healthy and disease controls. One-way ANOVA with Dunn's multiple comparison test is significant ($p<0.05$) for ALS vs HC and ALS vs DC, but not HC vs DC. C3 was also significantly increased in ALS versus healthy controls and DC versus HC, but not ALS versus DC (FIG. 15b). There were no significant alterations ($p>0.05$) across the subject groups for CRP or Tau using the same statistical tests.

A cut-off level of 0.635 ng/ml for pNFH generated a sensitivity of 84.4% sensitivity and 93.5% specificity for ALS in the training set (Table 4). All healthy control subjects exhibited minimal pNFH in the CSF and were below this cut-off value. Among the six disease controls that exhibited pNFH higher than the cut-off value included two subjects with metastatic brain tumors, one with progressive muscular atrophy, one with neurosarcoidosis, one subject with MS and one with multifocal motor neuropathy with conduction block. For C3, a threshold value of 3.62 µg/ml produced a sensitivity of 62% and specificity of 56% for ALS. Increasing the threshold value to 3.99 µg/ml reduced the sensitivity to 50% but increased the specificity to 71%. For CRP, a threshold of 3.2 ng/ml produced a sensitivity of 55% and specificity of 50%. A cut-off value of 240 pg/ml for total tau produced a sensitivity of 50% and specificity of 51%.

As C3 and CRP are involved in inflammatory responses, ALS and disease controls were distinguished by combining data from cytoskeletal and inflammatory pathways. Ratios of pNFH/C3, pNFH/CRP and pNFH/Total protein were calculated for each subject (FIG. 16). The pNFH/Total protein ratio demonstrated a similar pattern to pNFH alone indicating that there is an increase in absolute concentration of pNFH levels that change rather than a global increase in protein concentration. Interestingly, pNFH/C3 ratio levels showed significant differences ($p<0.05$ with one-way ANOVA and a Dunn's multiple comparison test) with less overlap between ALS and both disease controls and healthy control groups. This was also observed by the pNFH/CRP ratio levels ($p<0.05$), suggesting that inclusion of general inflammatory responses allows more specificity in identifying ALS (FIG. 16). It is noted that calculating the pNFH/CRP ratio can be problematic when levels of CRP are below the detection threshold. For such cases, they were recorded as positive (Minimal level above the detection threshold).

Receptor Operator Characteristic (ROC) curves were generated for pNFH, pNFH/C3 and pNFH/CRP. The area under the curve (AUROC) values were 0.9401, 0.9581 and 0.8406 respectively (FIG. 17). The ROC curves enabled optimum thresholds to be established for each of the variables in order to maximize the sensitivity and specificity. When determining thresholds, there is always a trade-off between sensitivity and specificity. This is highlighted in Table 4 using different threshold cut-off values for pNFH/C3. The optimal cut-off values were: pNFH/C3>0.000125 and pNFH/CRP>0.3755. Rules were also combined using either an AND function or an OR function. The former tends to increase specificity whereas the latter increases sensitivity. The majority of rules generated sensitivity>80% and specificity>90%, with the optimal rule a combination of pNFH and pNFH/C3 ratio levels (Table 4).

Together, these results demonstrate that pNFH achieves an excellent level of sensitivity and specificity, similar to findings from other laboratories (Brettschneider, J., et al., Neurology, 66:852-856 (2006); Reijn, T. S., et al., J Neurol, 256: 615-619 (2009)). For subjects above the pNFH cut-off value, the pNFH/C3 ratio threshold value increases confidence in the diagnosis of ALS. Combining the pNFH cut-off value, the pNFH/C3 ratio and the pNFH/CRP ratio provided 100% specificity in our training set, though the sensitivity for ALS was reduced to 59% (Table 4).

The data was verified using a separate test set of samples obtained from a different clinic but collected with the same procedures (Table 3B). pNFH and C3 levels were measured in all test subjects. A similar pattern was observed in this patient cohort, giving us greater confidence in both pNFH and pNFH/C3 in distinguishing ALS from controls. Using the threshold values determined by the ROC curves for the training set, a sensitivity of 95% and specificity of 93% for pNFH alone and a sensitivity of 96% and specificity of 90% for the pNFH/C3 ratio were obtained.

Finally, both sets of data were pooled to obtain more overall values for sensitivity and specificity across all subjects (FIG. 18). For pNFH>0.635, a sensitivity of 87.7% and specificity of 93.7% is achieved. For pNFH/C3>0.000125, a sensitivity of 92.3% and specificity of 89.2% is achieved. This is further illustrated in FIG. 19 which shows a scatter plot of pNFH and C3 values for each subject. The thresholds for pNFH and pNFH/C3 determined by the ROC curves are overlayed on the graph. The increased sensitivity of pNFH/C3 is reflected by ALS cases lying below the pNFH=0.635 threshold but above the pNFH/C3=0.000125 line. Six out of fourteen ALS mimics exhibited a false positive result when testing for pNFH/C3 alone as compared to just two out of fourteen when the pNFH threshold value was used in combination with pNFH/C3. A combined rule of pNFH>0.6349 ng/ml AND pNFH/C3>0.000125 generated a sensitivity of 87.7% and a specificity of 94.6%.

Figure 20:
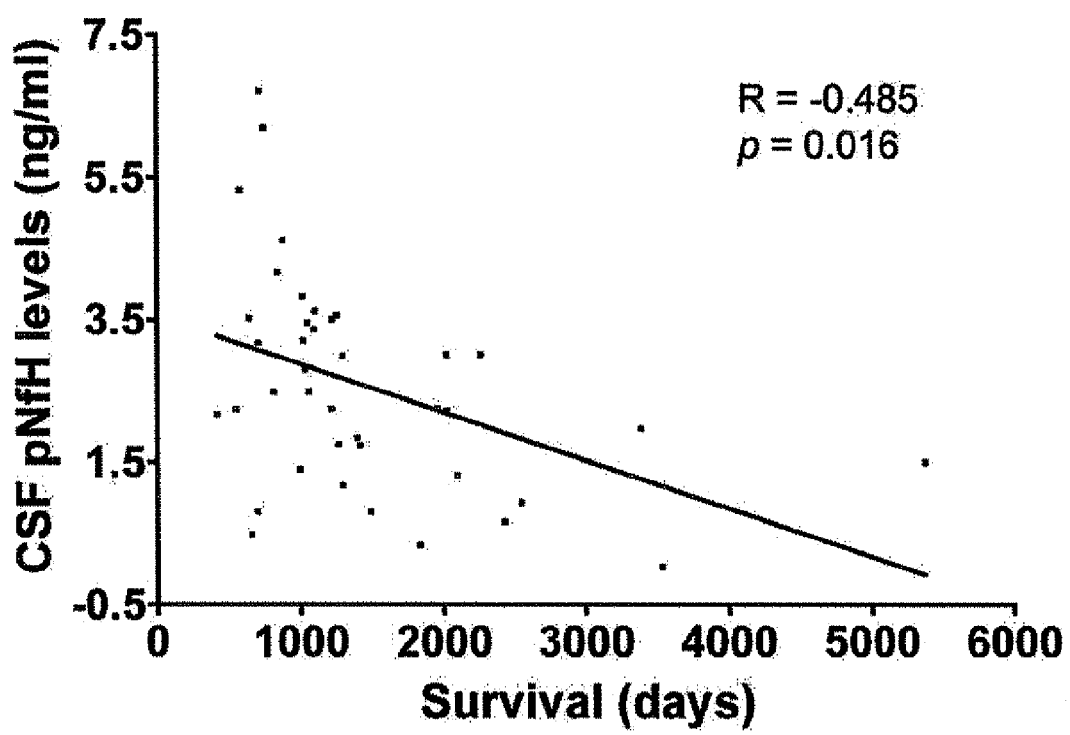
FIG. 20 shows an inverse correlation was seen between CSF pNFH levels (ng/ml) and survival (days) from symptom onset (days). Pearson test (R=-0.485, p=0.016).

Survival data for 39 ALS subjects. A correlation (Pearson test R=−0.485, p=0.016) was observed between pNFH levels and days from symptom onset to death (FIG. 20). The date of symptom onset was determined retrospectively by patient report. This result suggests that pNFH levels are a candidate prognostic biomarker. One ALS patient with a slow progressive form of the disease for which symptoms were confined to one hand had the longest survival, this patient had a low pNFH level.

While CSF is an excellent biofluid for biomarker discovery efforts due to its proximity to the affected nervous system tissue, it presents practical difficulties in terms of acquisition and potential risks to the patient. Therefore, matching plasma samples were examined to determine if similar pNFH alterations can be seen in plasma samples. With a sample size of 61 subjects, a significant increase (p<0.05) was detected using a one-way ANOVA with Dunn's multiple comparison test in pNFH level when comparing ALS versus HC (FIG. 21a). The median levels of pNFH detected in each subject group were 0.052 ng/ml for HC, 0.067 ng/ml for DC, and 0.08 ng/ml for ALS. pNFH levels between the CSF and plasma were compared for each individual subject. A correlation between the plasma and CSF pNFH levels was found, Spearman's rank correlation $R^2=0.18$, $p<0.001$ (FIG. 21b).

TABLE 3

Demographics of training and test sets

| Disease group | ALS | DC | HC |
|---|---|---|---|
| A) Training Set | | | |
| N | 45 | 25 | 36 |
| Sex: M:F | 32:13 | 13:12 | 13:23 |
| Age (Mean +/− St. Dev) | 55.0 +/− 13.4 | 47.9 +/− 15.4 | 46.8 +/− 15.6 |
| Site of onset Bulbar:Spine | 7:37 (1 cognitive onset) | N/A | N/A |
| Median Disease duration | 15.2 months | N/A | N/A |
| B) Test set | | | |
| N | 26 | 27 | 4 |
| Sex M:F | 11:9 | 16:11 | 2:2 |
| Age (Mean +/− St. Dev) | 55.1 +/− 13.8 | 54.1 +/− 14.7 | 45.3 +/− 20.0 |
| Bulbar:Limb | 5:21 | N/A | N/A |
| Median Disease duration | 17.8 months | N/A | N/A |

TABLE 4

Rules for diagnosing ALS generated using the training set.

| Rule | Sensitivity | Specificity |
|---|---|---|
| pNFH > 0.635 | 84.4% | 93.5% |
| pNFH/C3 > 0.000125 | 91.1% | 88.7% |
| pNFH/C3 > 0.21 | 77.8% | 95.2% |
| pNFH/CRP > 0.3755 | 61.4% | 87.1% |
| pNFH > 0.635 AND pNFH/C3 > 0.000125 | 84.4% | 95.2% |
| pNFH/C3 > 0.00021 AND pNFH/CRP > 0.3755 | 52.2% | 100% |
| pNFH/C3 > 0.00021 OR pNFH/CRP > 0.3755 | 86.4% | 83.9% |
| pNFH > 0.635 AND pNFH/C3 > 0.000125 AND pNFH/CRP > 0.3755 | 59.1% | 100% |

Rules highlighted in bold represent those to be considered in further validation studies.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for selecting a subject for treatment of amyotrophic lateral sclerosis (ALS) comprising
    measuring the concentration of phosphorylated neurofilament heavy chain (pNFH) in a blood or cerebral spinal fluid sample obtained from the subject;
    measuring the concentrations of complement C3 (C3) in the sample;
    determining a ratio of pNFH to C3; and
    selecting the subject for treatment if the ratio of pNFH/C3 is greater than 0.000125 and the concentration of pNFH is greater than 0.635 ng/ml,
    wherein the concentrations of pNFH and C3 are measured by immunoassay or mass spectrometric measures.

2. The method of claim 1 further comprising the step of administering a treatment to the patient.

3. The method of claim 1 wherein the concentration of pNFH and C3 are measured by ELISA.

4. The method of claim 1 wherein the concentration of pNFH and C3 are measured by mass spectrometric measures including Surface Enhanced Laser Dissociation/Ionization Time-of-Flight Mass Spectroscopy (SELDI-TOF-MS) or Liquid Chromatography-Mass Spectroscopy/Mass Spectroscopy (LS-MS/MS).

5. The method of claim 1 wherein the specificity of the method for selecting the subject with ALS is at least 95%.

6. A method for assisting in diagnosing amyotrophic lateral sclerosis (ALS) in a subject comprising:
    measuring the concentration of phosphorylated neurofilament heavy chain (pNFH) in a blood or cerebral spinal fluid sample obtained from the subject;
    measuring the concentration of complement C3 (C3) in the sample;
    measuring the concentration of C Reactive Protein (CRP) in the sample;
    determining a ratio of pNFH to C3;
    determining a ratio of pNFH to CRP;
    wherein a concentration of pNFH greater than 0.635 ng/ml and a ratio of pNFH/C3 greater than 0.000125 and a ratio of pNFH/CRP greater than 0.3755 is indicative of ALS,
    wherein the concentrations of pNFH, C3, and CRP are measured by immunoassay or mass spectrometric measures.

7. The method of claim 6 wherein the concentration of pNFH, C3, and CRP are measured by ELISA.

8. The method of claim 6 wherein the concentration of pNFH, C3, and CRP are measured by mass spectrometric measures including Surface Enhanced Laser Dissociation/Ionization Time-of-Flight Mass Spectroscopy (SELDI-TOF-MS) or Liquid Chromatography-Mass Spectroscopy/Mass Spectroscopy (LS-MS/MS).

9. The method of claim 6 wherein the specificity of the method for diagnosing the subject with ALS is about 100%.

10. A method for selecting a subject for treatment of amyotrophic lateral sclerosis (ALS) comprising:
    measuring the concentration of phosphorylated neurofilament heavy chain (pNFH) in a blood or cerebral spinal fluid sample obtained from the subject;
    measuring the concentration of complement C3 (C3) in the sample
    measuring the concentration of C Reactive Protein (CRP) in the sample,
    determining a ratio of pNFH to C3;
    determining a ratio of pNFH to CRP;

selecting the subject for treatment when the concentration of pNFH is greater than 0.635 ng/ml and the ratio pNFH/C3 is greater than 0.000125 and the ratio of pNFH/CRP is greater than 0.3755 is indicative of ALS,
wherein the concentrations of pNFH, C3, and CRP are measured by immunoassay or mass spectrometric measures.

11. The method of claim 10 wherein the concentration of pNFH, C3, and CRP are measured by ELISA.

12. The method of claim 10 wherein the concentration of pNFH, C3, and CRP are measured by mass spectrometric measures including Surface Enhanced Laser Dissociation/Ionization Time-of-Flight Mass Spectroscopy (SELDI-TOF-MS) or Liquid Chromatography-Mass Spectroscopy/Mass Spectroscopy (LS-MS/MS).

13. The method of claim 10 wherein the specificity of the method for selecting a subject with ALS is about 100%.

14. A method for assisting in diagnosing amyotrophic lateral sclerosis (ALS) in a subject comprising:
measuring the concentrations of phosphorylated neurofilament heavy chain (pNFH) in a blood or cerebral spinal fluid sample obtained from the subject;
measuring the concentration of complement C3 (C3) in the sample;
determining a ratio of pNFH to C3,
wherein a ratio greater than 0.000125 is indicative of ALS,
wherein the concentrations of pNFH and C3 are measured by immunoassay or mass spectrometric measures.

15. The method of claim 14 wherein the concentration of pNFH and C3 are measured by ELISA.

16. The method of claim 14 wherein the concentration of pNFH and C3 are measured by mass spectrometric measures including Surface Enhanced Laser Dissociation/Ionization Time-of-Flight Mass Spectroscopy (SELDI-TOF-MS) or Liquid Chromatography-Mass Spectroscopy/Mass Spectroscopy (LS-MS/MS).

17. The method of claim 14 wherein the specificity of the method for diagnosing the subject with ALS is at least 95%.

18. A method for assessing the efficacy of a treatment for amyotrophic lateral sclerosis (ALS) comprising
administering a drug to a subject having ALS,
measuring the concentrations of pNFH and complement C3 (C3) in a blood or cerebrospinal fluid sample obtained from the subject before and after administration of the drug;
wherein the treatment is effective if the ratio of pNFH to C3 decreases after administration of the drug relative to the ratio of pNFH to C3 prior to administration of the drug,
wherein the concentrations of pNFH and C3 are measured by immunoassay or mass spectrometric measures.

19. The method of claim 18 wherein the concentration of pNFH and C3 are measured by ELISA.

20. The method of claim 18 wherein the concentration of pNFH and C3 are measured by mass spectrometric measures including Surface Enhanced Laser Dissociation/Ionization Time-of-Flight Mass Spectroscopy (SELDI-TOF-MS).

21. A method for assisting in diagnosing amyotrophic lateral sclerosis (ALS) in a subject comprising:
measuring the concentration of phosphorylated neurofilament heavy chain (pNFH) in a blood or cerebral spinal fluid sample obtained from the subject;
measuring the concentration of complement C3 (C3) in the sample;
measuring the concentration of C Reactive Protein (CRP) in the sample;
determining a ratio of pNFH to C3;
determining a ratio of pNFH to CRP;
wherein a concentration of pNFH greater than 0.635 ng/ml, and a ratio of pNFH/C3 greater than 0.000125, or a ratio of pNFH/CRP greater than 0.3755 is indicative of ALS,
wherein the concentrations of pNFH, C3, and CRP are measured by immunoassay or mass spectrometric measures.

* * * * *

UNITED STATES PATENT AND TRADEMARK OFFICE
CERTIFICATE OF CORRECTION

PATENT NO. : 8,465,727 B2  Page 1 of 1
APPLICATION NO. : 12/899235
DATED : June 18, 2013
INVENTOR(S) : Robert P. Bowser It is certified that error appears in the above-identified patent and that said Letters Patent is hereby corrected as shown below:

In the Claims
Claim 1, column 24, line 10, replace "concentrations" with --concentration--.
Claim 1, column 24, line 15, replace "ng/ml," with --ng/ml, and--.
Claim 6, column 24, line 39, replace "C3;" with --C3; and--.
Claim 6, column 24, line 43, replace "ALS," with --ALS, and--.
Claim 10, column 24, line 63, replace "sample" with --sample;--.
Claim 10, column 24, line 65, replace "sample," with --sample;--.
Claim 10, column 24, line 67, replace "CRP;" with --CRP; and--.
Claim 10, column 25, line 4, replace "ALS," with --ALS, and--.
Claim 14, column 25, line 25, replace "C3," with --C3; and--.
Claim 14, column 25, line 26, replace "ALS," with --ALS, and--.
Claim 18, column 26, line 3, replace "ALS," with --ALS, and--.
Claim 18, column 26, line 10, replace "drug," with --drug, and--.
Claim 21, column 26, line 30, replace "CRP;" with --CRP; and--.
Claim 21, column 26, line 33, replace "ALS," with --ALS, and--.

Signed and Sealed this
Twenty-seventh Day of May, 2014

Michelle K. Lee
*Deputy Director of the United States Patent and Trademark Office*